United States Patent [19]
Zhang

[11] Patent Number: 5,578,486
[45] Date of Patent: Nov. 26, 1996

[54] RECOMBINANT MICROBIAL FERTILIZER AND METHODS FOR ITS PRODUCTION

[75] Inventor: Ling Y. Zhang, Rockville, Md.

[73] Assignee: International TLB Research Institute, Inc., Poolesville, Md.

[21] Appl. No.: 286,470

[22] Filed: Aug. 5, 1994

[51] Int. Cl.$^6$ .............................. C12N 1/00; C05F 11/08
[52] U.S. Cl. ............................. 435/243; 71/7; 435/252.1; 435/252.3; 435/252.4
[58] Field of Search ........................... 71/6, 7; 504/117; 435/243, 252.35, 252.4, 254.21, 252.3

[56] References Cited

U.S. PATENT DOCUMENTS

| | | | |
|---|---|---|---|
| 4,119,429 | 10/1978 | Lovness | 71/6 |
| 4,952,229 | 8/1990 | Muir | 71/7 |

FOREIGN PATENT DOCUMENTS

| | | | |
|---|---|---|---|
| 553377A1 | 1/1992 | European Pat. Off. | |
| WO93/14791 | 8/1993 | WIPO | |

OTHER PUBLICATIONS

Mba, C. C., "Field Studies on Two Rock Phosphate Solubiizing Actinomycete Isolates as Biofertilizewr Sources," *Environmental Manager*, 17(2):263–269 (1994).

Bohlool, B. B., et al., "Biological Nitrogen Fixation for Sustainable Agriculture: A Perspective." *Plant and Soil*, 141:1–11 (1992).

Bhanavase, D. B., et al., "Nodulation and Nitrogen Fixation as Influenced by Micronutrients—A Review," *J. Maharashtra Agric Univ*, 18(2):167–174 (1993).

Babu, C. R., et al., "Biological Nitrogen Fixation Technologies for Ecological Rehabilitation of Degraded Soils and Natural Ecosystems," *Proc. Indian Natn. Sci. Acad.*, B59 (3)(4):359–366 (1993).

Gaur, Y. D., "Microbiology, Physiology and Agronomy of Nitrogen Fixation: Legume–Rhizobium Symbiosis," *Proc. Indian Natn. Sci. Acad.*, B59 (3)(4):333–358 (1993).

Gilland, B., "Cereals, Nitrogen and Population: An Assessment of the Global Trends," *Endeavour, New Series,*, 17(2):pp. 84–88 (1993).

Lau–Wong, M. M., "Field Testing of the Effectiveness of Bacterial Fertilizer in Nepal," *Agriculture, Ecosystems and Environment* 19:145–153 (1987).

Oertli, J. J., "Controlled–Release Fertilizers," *Fertilizer Research* 1:103–123 (1980).

Gallon, J. R., "Tansley Review No. 44, Reconciling the Incompatible: $N_2$ Fixation and $O_2$", *New Phytol.* 122:571–609 (1992).

Fisk, H., et al., "Direct Gene Transfer Technology and Progress: The Introduction and Expression of Transgenes in Plants," *Scientia Horticulturae* 55:5–36 (1993).

Segal, Wm., et al., "Extent of Regeneration of the Microbial Community in Reclaimed Spent Oil Shale Land," *J. Environ. Qual.* 16(1), pp. 44–48 (1987).

Tigerstedt, P. M. A., "Genetic Adaptation of Plants in the Subartic Environment," *Holacrctic Ecology* 2:264–268 Copenhagen (1979).

Obeng–Asamoa, E. K., et al., "Periphyton i the Volta Lake. I. Seasonal Changes on the Trunks of Flooded Trees," *Hydrobiologia* 76:191–200 (1980).

Anderstam, B., et al., "Studies of Possible Genetic Effects in Bacteria of High Frequency Electromagnetic Fields," *Hereditas* 98:11–32 (1983).

Lin, Lung–Shen, et al., "Isolation of Restriction Deficient Mutant for *Corynebacterium Glutamicum* by Electroporation," *Biotechnology Techniques* 7(11) 823–626 (1993).

Rosado, A., et al., "Optimization of Electroporation Procedure to Transform *B. polymyxa* SCE2 and other Nitrogen––Fixing Bacillus," *Journal of Microbiological Methods*, 19:1–11 (1994).

Hamnerius, Y., "Exposure Systems for Studies of the Effects of Electromagnetic Fields on Biological Systems," *Hereditas* 98:43–59 (1983).

Primary Examiner—Nancy T. Vogel
Assistant Examiner—Terry A. McKelvey
Attorney, Agent, or Firm—Howrey & Simon; Jeffrey I. Auerbach

[57] ABSTRACT

A microbial fertilizer that constitutes a symbiotic association of several recombinant microbial species is described. The fertilizer contains four streptomyces strains and two yeast strains. The streptomyces strains include a nitrogen fixing strain, a phosphorus decomposer, a potassium decomposer and a coal waste decomposer. The yeast strains produce growth factors and energy required by the streptomyces.

12 Claims, 7 Drawing Sheets

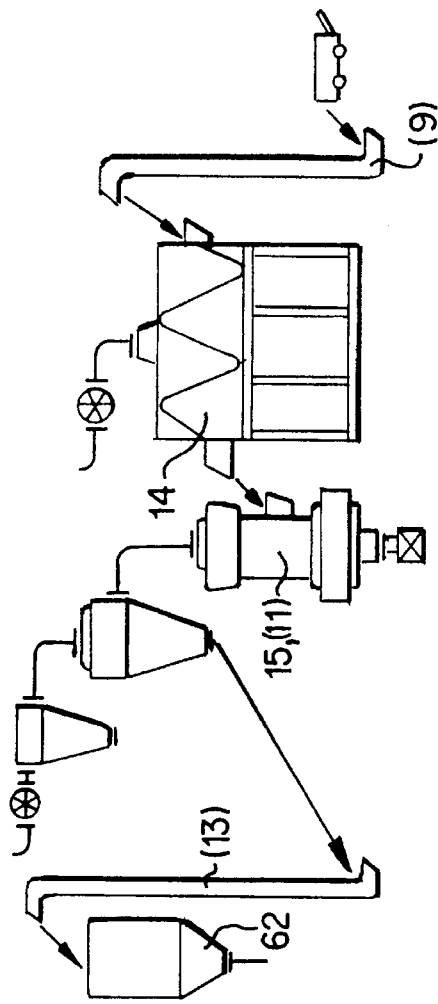
FIG. 4C
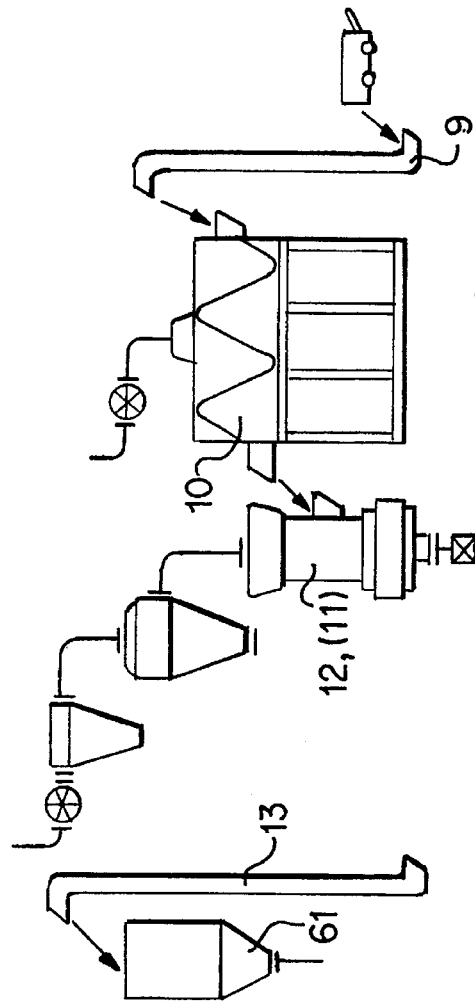
FIG. 4B
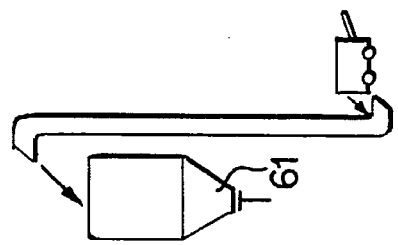

RECOMBINANT MICROBIAL FERTILIZER AND METHODS FOR ITS PRODUCTION

FIELD OF THE INVENTION

The present invention relates to a microbial fertilizer that comprises a symbiotic association of several recombinant microbial species. The fertilizer is capable of fixing atmospheric nitrogen, and of organifying phosphate and potassium so that these nutrients can be utilized by plants. The invention pertains to the recombinant microbes, to methods of producing them, to the fertilizer, and to methods of producing the fertilizer.

BACKGROUND OF THE INVENTION

Historically, the production of foodstuffs needed to support the continuing increase in global population has thus far been accomplished by increasing the total acreage under cultivation and by augmenting crop yields through the use of fertilizers. The expansion of cropland, however, essentially ceased years ago (Gilland, B., *Endeavor* 17:84–88 (1993)).

The continued increase in crop yields (a 250% increase in world cereal grain yield from 1950 to 1990) has been obtained by expanding and improving irrigation systems, by protecting crops from disease, insects, and the competition of weeds, and by the development of new varieties of plants (Gilland, B., *Endeavor* 17:84–88 (1993), see, Bohtool, B. B. et al., *Plant Soil* 141:1–11 (1992)). The application of increasing amounts of chemical fertilizers (nitrogen, phosphorus and potassium) was an important factor in this "Green Revolution."

Nitrogen is required in all protein, and is the most important of all plant nutrients. Nitrogenous fertilizers are derived from ammonia, which is produced from natural gas. Because chemical nitrogen fertilizers are produced from an energy source, its price is sensitive to fluctuations in world energy prices. Ammonia is often used as a fertilizer in more developed countries. The compound is hazardous, and must be stored as a gas and applied to fields under pressure. In much of the world, ammonia is converted into urea for use as a fertilizer. Although significant energy is required for this reaction, urea can be pelleted or powdered, and thus can be transported and handled more easily than ammonia.

Phosphorus is important for plant growth and seed formation. The phosphorus of chemical fertilizers is derived from "phosphate rock," which normally contains about 20–40% $P_2O_5$. Unfortunately, $P_2O_5$ is not water soluble, and thus the phosphate of $P_2O_5$ is not readily accessible to plants. Thus, phosphate rock must generally be processed into a water soluble form (e.g., ammonium phosphate). Such processing requires the production, storage and handling of highly corrosive phosphoric acid intermediates.

Potassium is the least expensive of the common fertilizer. It is obtained from the mining of "potash," and does not require chemical processing. Potassium chloride (muriate of potash) comprises over 90% of the potash that is mined. The remaining potashes are chiefly potassium sulfate and nitrate.

Several factors indicate that chemical fertilizer production will not be able to support future increases in crop yield (Bohtool, B. B. et al., *Plant Soil* 141:1–11 (1992)). Substantial energy is needed to produce nitrogen fertilizers. It has been estimated that 1.3% of world energy consumption is needed to produce existing stores of nitrogen based fertilizers (Gilland, B., *Endeavor* 17:84–88 (1993)). As world population grows, the price and availability of energy is thus likely to have a significant impact on the production of nitrogen fertilizers. Irrigation and rain water "run-off" and leaching of applied fertilizers cause the eutrophication of lakes, rivers, and bays, and thus substantially contribute to water pollution. Such pollution will only be exacerbated by an even wider application of fertilizers.

Several approaches have been taken in the hope of improving the economics of fertilizer use and of lessening the adverse ecological effects of fertilizers. One approach concerns the use of "controlled release" formulations. Increased crop yields can be expected if the rate of nutrient supply is adapted to the physiological needs of the crop (Oertli, J. J., *Fertil. Res.* 1:103–123 (1980)). By providing a season's nutritional requirements in a single application, soil compaction is reduced, there is less mechanical damage to crops, and a savings in labor can be realized.

Premature dissolution of water-soluble fertilizers has been regulated by granulating the fertilizers and coating the granules with a diffusion barrier (Oertli, J. J., *Fertil. Res.* 1:103–123 (1980)). A variety of suitable coatings has been described. Osmocote, for example, is a co-polymer of dicyclopentadiene and an oil derived from soybean or linseed (Jung, J. et al., In: *Die Landwirtschaftliche Versuchsstation Limbergerhof* (1914–1964), Herausg. Badische & Soda-Fabrik, Ludwigshafen, Landwirtschaftliche abt., pp. 164–182 (1964)). When the granules take up water, the fertilizer salts dissolve, generating a high internal hydrostatic pressure that presses the nutrients out of the granule.

Molten sulfur has also been used as a coating material (Jarrell, W. M. et al., *Soil Sci. Soc. Amer. J.* 43602–605 (1979); (Jarrell, W. M. et al., *Soil Sci. Soc. Amer. J.* 431044–1050 (1979)). The granules may contain a microbicide to retard microbial growth, and a wax or petroleum-based sealant to retard dissolution. A conditioner (i.e., kaolinite, diatomaceous earth, or vermiculite) is added to the final granule in order to prevent granule self adhesion.

Controlled release has been accomplished by formulating the fertilizer with nutrients that are in the form of sparingly soluble compounds. Dissolution of the compound by the plant shifts the controlling equilibrium such that more of the compound dissolves. Metals, such as iron or magnesium have also been used to shift the equilibrium of dissolution, thereby altering the rate of release.

Various organic molecules (i.e., urea formaldehyde polymers, isobutylidenediureas, crotonylidenediureas, acetaldehyde-urea) have also been used to control nutrient release rates (Oertli, J. J., *Fertil. Res.* 1:103–123 (1980)).

Microbial fertilizers have been proposed as an alternative to chemical fertilizers (Giller K. E. et al., In: *Nitrogen Fixation in Tropical Cropping Systems*, Ocon:C.A.B. International (1991); Babu, C. R. et al., *Proc. Indian Nat'l. Sci. Acad.* B59:359–366 (1993)). Several genera of bacteria (collectively termed "rhizobia" are capable of fixing atmospheric nitrogen into nitrates or ammonia. The rhizobia form tubercles (or nodules) within the roots of plants. These nodules comprise a symbiotic relationship between the rhizobia and the plant, in which the rhizobia provides reduced nitrogen in return for other nutrients provided by the plant (Guar, Y. D., *Proc. Indian Nat'l. Sci. Acad.* B59:333–358 (1993)). Unfortunately, rhizobia are essentially unable to colonize certain economically important classes of plants (such as the cereals, grasses, fruit trees, etc.). Efforts to provide nitrogen to cereals by mixed cultivation with nodulated legumes has been largely unsuccessful (Guar, Y. D., *Proc. Indian Nat'l. Sci. Acad.* B59:333–358 (1993)). Moreover, the high cost of present microbial fertilizers renders their use economically unfeasible.

Stains of Actinomycetes and Bacillus have been isolated that can solubilize the phosphorus of rock phosphorus, and their use in providing phosphates to crops has been attempted (Banik, S. et al., *Zentralblatt für Bakteriologie: Abteilung* 136:478–486 (1981); Banik, S. et al., *Plant Soil* 69:353–364 (1982); see also MBA, C. C., *Exper. Manag.* 18:257–261 (1994) and MBA, C.C., *Exper. Manag.* 18:263–269 (1994)).

The possibility of using nitrogen fixing bacteria as fertilizers has been complicated by the ecological constraints encountered in attempting to establish a non-native bacteria within an existing ecosystem (Bohtool, B. B. et al., *Plant Soil* 141:1–11 (1992)). These factors include the competitive ability of the nitrogen fixing bacteria, the magnitude of the naturally occurring soil genera, etc. (Babu, C. R. et al., *Proc. Indian Nat'l. Sci. Acad.* B59:359–366 (1993)). In addition, the presence and concentration of micronutrients (such as copper, iron, molybdenum, zinc, manganese and boron) affect the capacity of microbial fertilizers to colonize root nodules and mediate nitrogen fixation (Bhanavase, D. B. et al., *J. Maharashtra Agric. Univ.* 18:167–174 (1993)). A nitrogen-fixing Azotobacter species has been used to provide nitrogen to rice, wheat and maize (LauWong, M. M., *Agric. Ecosys. Environ* 19:145–153 (1987)). The trials demonstrated a statistically significant effect for rice, however, no significant effect was observed for wheat or maize (Lau-Wong, M. M., *Agric. Ecosys. Environ* 19:145–153 (1987)).

In view of the importance of an alternative to the use of chemical fertilizers, it would be desirable to have a biological fertilizer which would not damage the environment, and which could be employed in an economically feasible manner. The present invention provides such a fertilizer, as well as methods for its use.

SUMMARY OF THE INVENTION

The present invention relates to a microbial fertilizer that comprises a symbiotic association of several recombinant microbial species. Specifically, the fertilizer contains four streptomyces strains and two yeast strains. The streptomyces strains include a nitrogen fixing strain, a phosphorus decomposer, a potassium decomposer and a coal waste decomposer. The yeast strains produce growth factors and energy required by the streptomyces.

In detail, the invention provides a microbial fertilizer that comprises:

(a) nitrogen fixing bacterium;

(b) carbon-waste decomposing bacterium;

(c) phosphate rock decomposing bacterium; and (d) rock potassium decomposing bacterium; wherein the bacteria produce phosphate, potassium, and reduced nitrogen nutrients in amounts that augment the growth of plants. The invention further concerns a microbial fertilizer that additionally contains:

(e) a growth factor producing yeast; and (f) an energy producing yeast.

The invention also provides such a fertilizer, wherein the fertilizer comprises a granule that comprises:

(A) a central rock phosphate core, wherein the core additionally contains the phosphate rock decomposing bacterium (c);

(B) an intermediate layer comprising a carbonaceous material and fermented bran, wherein the intermediate layer additionally contains the nitrogen fixing bacterium (a), the carbon-waste decomposing bacterium (b), the rock potassium decomposing bacterium (d), the energy producing yeast (e), and the growth factor producing yeast (f); and (C) an outer film comprising bone glue and powdered talc.

The invention particularly concerns such microbial fertilizers wherein the nitrogen fixing bacterium (a) is a *Streptomyces jingyangensis* of ATCC 55597 that fixes nitrogen, and that contains DNA of *Alcaligenes faecalis*; wherein the carbon-waste decomposing bacterium (b) is a *Streptomyces jingyangensis* of ATCC 55597 that decomposes carbon-waste, and that contains DNA from *Polyangium cellulosum*; wherein the phosphate rock decomposing bacterium (c) is a *Streptomyces jingyangensis* of ATCC 55597 that decomposes phosphate rock, and that contains DNA from *Bacillus megaterium phosphaticum*; and/or wherein the rock potassium decomposing bacterium (d) is a *Streptomyces jingyangensis* of ATCC 55597 that decomposes rock potassium, and that contains DNA from *Bacillus mucilagenosus* var. Krassilnikov.

The invention further concerns such microbial fertilizers wherein the growth factor producing yeast (e) is *Saccharomyces diastaticus* of ATCC 55597 and/or the energy producing yeast (f) is *Saccharomyces sinenses* Yue of ATCC 55597.

The invention concerns the microbial fertilizer, ATCC 55597.

The invention also concerns the *Streptomyces jingyangensis* bacterium of ATCC 55597 that fixes nitrogen, and that contains DNA of *Alcaligenes faecalis*, the *Streptomyces jingyangensis* bacterium of ATCC 55597 that decomposes carbon-waste, and that contains DNA from *Polyangium cellulosum*, the *Streptomyces jingyangensis* bacterium of ATCC 55597 that decomposes phosphate rock, and that contains DNA from *Bacillus megaterium phosphaticum*, the *Streptomyces jingyangensis* bacterium of ATCC 55597 that decomposes rock potassium, and that contains DNA from *Bacillus mucilagneosus* var. Krassilnikov, the growth factor producing yeast, *Saccharomyces diastaticus*, of ATCC 55597, and the energy producing yeast, *Saccharomyces sinenses* Yue, of ATCC 55597.

The invention particularly concerns such microbial fertilizers, wherein the central rock phosphate core is manufactured by the steps:

(1) grinding rock phosphate to about 200 mesh;

(2) combining the ground rock phosphate with wheat bran fermented by the growth factor producing yeast, and with the rock phosphate decomposing bacterium to form a mixture of ground rock phosphate, the fermented bran, the growth factor producing yeast, and the rock phosphate decomposing bacterium;

(3) drying the mixture of step (2) and forming the dried mixture into granules;

and wherein the intermediate layer is manufactured by the steps:

(1') grinding weathered coal or coal-mine waste to about 200 mesh;

(2') combining the ground weathered coal or coal-waste with wheat bran fermented by the energy producing yeast, and with the nitrogen fixing bacterium, the carbon-waste decomposing bacterium, and the potassium rock decomposing bacterium to form a mixture of ground rock phosphate, fermented bran, the energy producing yeast, the nitrogen fixing bacterium, the carbon-waste decomposing bacterium, and the potassium rock decomposing bacterium;

(3') drying the mixture of step (2') and forming the dried mixture into a layer around the granules of step (3); and wherein the outer film is manufactured by spraying an aqueous solution of bone glue and powdered talc onto the surface of the intermediate layer formed in step (3').

The invention provides a method of augmenting crop yield of all growing plants, especially cereals, vegetables, fruits, and other grass crops.

BRIEF DESCRIPTION OF THE FIGURES

FIGS. 4A, 4B, 4C, 4D, 4E and 4F illustrate the equipment and apparatus used in the formation of the TLB microbial fertilizer.

DETAILED DESCRIPTION OF THE INVENTION

1. Overview of the TLB Fertilizer

Figure 1:
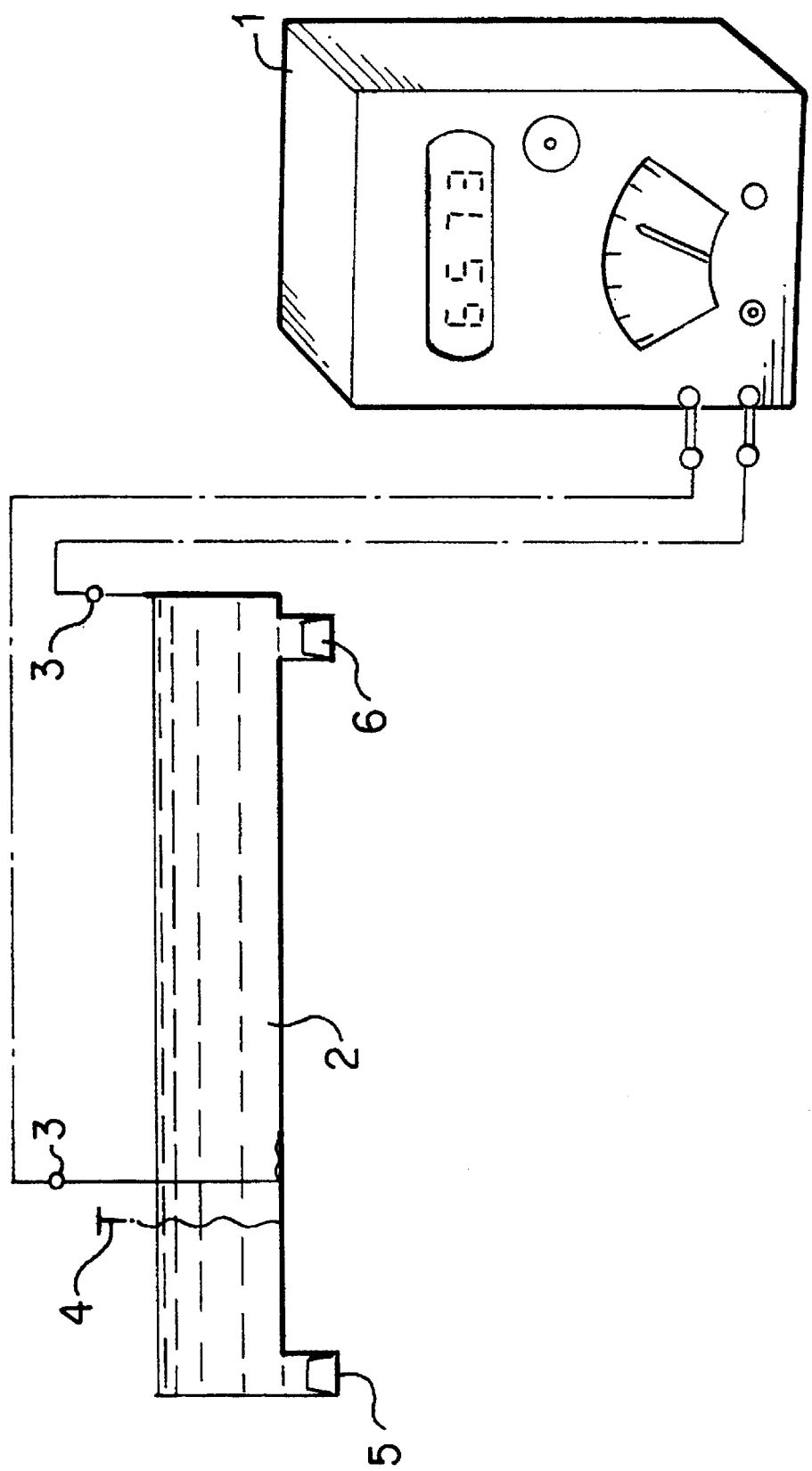
FIG. 1 is a schematic representation of an apparatus suitable for subjecting microorganisms to an EM field.

In the 78 years since its first appearance in 1915, chemical fertilizer has been used widely and has contributed greatly to human well-being by increasing agricultural yields. However, prolonged use of chemical fertilizers produces deleterious side-effects, such as reduction of soil fertility, hardening of soil, pollution of water and air, and decreasing plant quality, thereby causing harm to human health.

In order to solve the problem of chemical fertilizer pollution, many researchers in the United States, Japan, Germany, Australia and other countries have devoted substantial time and materials to finding a fertilizer which can replace chemical fertilizers. China began such research: in 1937 and obtained some success, for example, in inoculating wheat with nitrogen-fixing bacteria. Unfortunately, up to 100 grams of that bacterial agent needed to be used per one mu (666 $m^2$) of land. Thus, the bacteria was usable only as a supplemental fertilizer. At best it replaced only a small quantity of chemical fertilizer and thus cannot overcome or reverse the damage caused by chemical fertilizers.

The present invention arises from the construction of several recombinant bacterial strains that are capable of fixing nitrogen, decomposing rock phosphate and decomposing potassium. In a highly preferred embodiment, these bacterial strains are used in a microbial fertilizer, termed "TLB." The fertilizer is a complete fertilizer, and is composed of multiple microbial strains that function in a complex symbiotic relationship with one another.

The fertilizers of the present invention may be used to augment the growth of a wide variety of plants. As used herein, a fertilizer "augments" plant growth if its presence in the soil, or applied to the roots or leaves of the plants increases the viability, size, or rate of growth of the plant. The fertilizers of the present invention may be used to augment crop yield of any growing crops such as cereal crops, fruit crops, vegetable crops, and grass crops (such crops include, but are not limited to wheat, barley, soybean, rice, oat, apple, tomato, orange, cherry, melon, lettuce, potato, carrot, corn, fescues, tobacco, cotton, etc.).

In the most preferred embodiment, the microbial strains are incorporated into a unique multi-layered granule (the TLB fertilizer) which fosters the symbiotic relationship and provides high N-P-K values—equivalent to at least 46% N, 30% $P_2O_5$ and 20% $K_2O$ from conventional inorganic fertilizers—to crops and other plants. Importantly, the provided nutrients do not leach out, run off, or volatilize. Thus, one application can be used to provide all the nutrition needed for an entire growing season for most crops. The TLB fertilizer and methods for its manufacture are described in CN patent applications: 93109229.9; 93109230.2; 93109231.0 and 93114110.9, all herein incorporated by reference.

In its most preferred embodiment, the microbes of the TLB fertilizer comprise six microbial strains:

(1) a nitrogen-fixing strain;

(2) a phosphate decomposing strain;

(3) a potassium decomposing strain;

(4) a carbon decomposer (5) a growth-factor producing yeast strain; and (6) an energy producing yeast strain.

The nitrogen fixing strain and the phosphate, potassium and carbon decomposing strains are most preferably recombinant strains which have been engineered to exhibit increased activity.

The microbes of the TLB fertilizer form a symbiotic community of six different but mutually interdependent microbes. Five of these provide the conditions required for the life activity of the nitrogen-fixer bacterium. At the same time, the nitrogen-fixer provides the nitrogen nutrient required by three of the other five. The phosphorus- and potassium-decomposers, along with the carbon decomposing bacterium, provide the phosphorus, potassium, and the carbon nutrients needed by the nitrogen-fixer bacterium. The phosphorus- and potassium-decomposers provide the phosphorus and potassium required by the carbon decomposer and receive in return their carbon requirements. Alone, none of these engineered organisms can progress along its accelerated metabolic pathway and thus cannot survive as such outside its symbiotic community. The fifth TLB strain is a yeast producing growth factor for the nitrogen-, phosphorus-, and potassium decomposer bacteria. The sixth is a yeast supplying the energy (ATP) deficit incurred in the nitrogen-fixing process and decomposition processes.

A. The Genetic Manipulation of Agriculturally Important Microorganisms

The genetic manipulation of natural isolates is a highly complex process. In order to obtain improved nitrogen fixing, and phosphate, potassium and carbon decomposing strains, it was desirable to genetically modify natural ("wild-type") isolates that were capable of mediating such activities. Two problems have impeded prior efforts to accomplish this goal.

Soil is a complex culture medium, and the biological properties of microorganisms living there must accord with that environment. As is known, microorganisms in their natural environment often live in complex interactive systems composed of many species. No matter how many factors are taken into account in preparing artificial culture media, the result still falls far short of duplicating the environment found in the wild. As will be appreciated, artificial culture media must be used to isolate and culture the wild-type isolates. Such media differs, however, in composition from that of the soil, and thus introduces a selective pressure for bacteria that are better able to survive on laboratory medium. The consequence of such selective pressure is the fact that bacteria isolated on laboratory medium may be less capable of establishing itself when transplanted back into a natural environment. The problem of induced variation thus represents a serious obstacle to the genetic manipulation of free-living, wild-type isolates.

A second difficulty encountered in modifying natural isolates pertains to the uncharacterized nature of the genetic apparatus within such microbes. For example, conventional vectors may be incapable of replicating in the natural isolate. Similarly, the isolate may have one or more restriction endonucleases that may operate to degrade any introduced DNA.

One aspect of the present invention concerns the use of electromagnetic (EM) irradiation to suppress replication of undesired variants of the natural isolates. The presence of an electromagnetic field stimulates the proliferation of some bacteria while repressing that of others. The molecular mechanism responsible for such an effect is not well understood (Anderstam, B. et al., *Hereditas* 98:11–32 (1983)), but is not needed for the practice of the present invention. The rationale of the method lies in the fact that microorganisms placed in an electromagnetic field respond to changes in frequency and field potential; changes in these variables significantly affect microbial metabolism. An analogy is found in the differential responses of photomicrobes to various frequencies in the visible light spectrum. For example, different species of photomicrobes live at the 500 nm, 590 nm, 800 nm, 850 nm, and 900 nm wavelengths. Visible light is itself a segment of the EM spectrum.

Methods and apparatus for subjecting bacteria to electromagnetic fields are disclosed by Anderstam, B. et al. (*Hereditas* 98:11–32 (1983)), by Hamnerius, Y. (*Hereditas* 98:43–59 (1983), and particularly by Zhang, L. Y. (CN Patent Application Serial No. 94103474.7), all of which disclosures are herein incorporated by reference. Uses of EM to manipulate and sterilize bacteria are also discussed by Corner, A. (U.S. Pat. No. 5,288,471); Goodrich, R. P. et al. (PCT Patent Application WO93/14791); Bridges, J. E. (European Patent Application 533,377).

The present invention departs from such methods by providing a general approach for isolating, rather than eliminating, naturally occurring microbes (especially bacteria) that are present in a natural source. In accordance with the methods of the present invention, the source material, preferably a liquid, is introduced into a chamber that is bounded by immersed electrodes. A preferred example of such a chamber is shown in FIG. 1. With reference to FIG. 1, a source of EM field (1) is connected to electrodes (3) that are immersed in a chamber (2) containing the culture medium and microbial mixture that is to be processed. In a preferred embodiment, the chamber will have one or more drain valves (5, 6) at different positions in the chamber (5). The chamber will also preferably contain a flow valve (4) located external to the electrodes (3). In the most preferred embodiment, the EM field source (1) is tunable, such that fields of different frequency may be obtained.

The isolation chamber is made from, for example, 10–30 mm diameter glass tube. The electrodes can be either copper or silver- or gold-plated metal. The signal generator is a signal source commonly used in wire or wireless communications, having a wavelength range of 0.1 µm–1.0 mm. The output terminal is connected to the two electrodes of the isolation chamber by two coaxial cables.

The EM field created by the source (1) is a high frequency electromagnetic field induced by alternating voltage potentials. The source will be capable of inducing an EM field of wavelenths from 0.1 µm to 1.0 mm (corresponding to frequencies of 10 MHz to 1 kHz). In a preferred embodiment, the source (1) can be set to create wave amplitudes of from −0.5 V to 3.6 V.

In order to isolate a pure culture of a desired bacterium from a natural source, one fills the isolation chamber with a soil solution (soil filtrate) containing the microorganism to be isolated then insert a stopper to seal the chamber. The signal generator is turned on and the frequency and voltage are adjusted as required for the particular isolation procedure. The timer is adjusted for the time required by the particular isolation procedure. At the end of the required time, the field is left turned on, and the flow valves are closed tightly. The drain is opened and the desired microorganism is collected. Two or three repetitions of these steps will produce very pure cultures of the desired microorganisms.

For example, as described below, subjecting a naturally occuring mixture of bacteria that contains an Alcaligenes species to a field having a wavelength of 40–100 µm and a peak EMF of 20–80 mV for 2–10 hours will selectively enrich for that Alcaligenes species. In a similar fashion, microbes that can decompose carbon waste can be isolated from natural sources using a field having a wavelength of 160–230 µm and a peak EMF of 10–60 mV for 2–24 hours. Organisms that can decompose rock phosphate can be isolated using a field having a wavelength of 10–60 µm and a peak EMF of 10–30 mV for 2–16 hours. Organisms that can decompose potassium rock can be isolated using a field having a wavelength of 3–20 µm and a peak EMF of 21–110 mV for 2–24 hours. By routine manipulation of the field parameters, the isolation of any bacterium from a natural source or from a mixture of contaminants can be accomplished.

After such enrichment, the desired species may then be recovered from the chamber by manipulating the relevant flow control (4) and drain valves (5, 6) of the apparatus.

Figure 2:
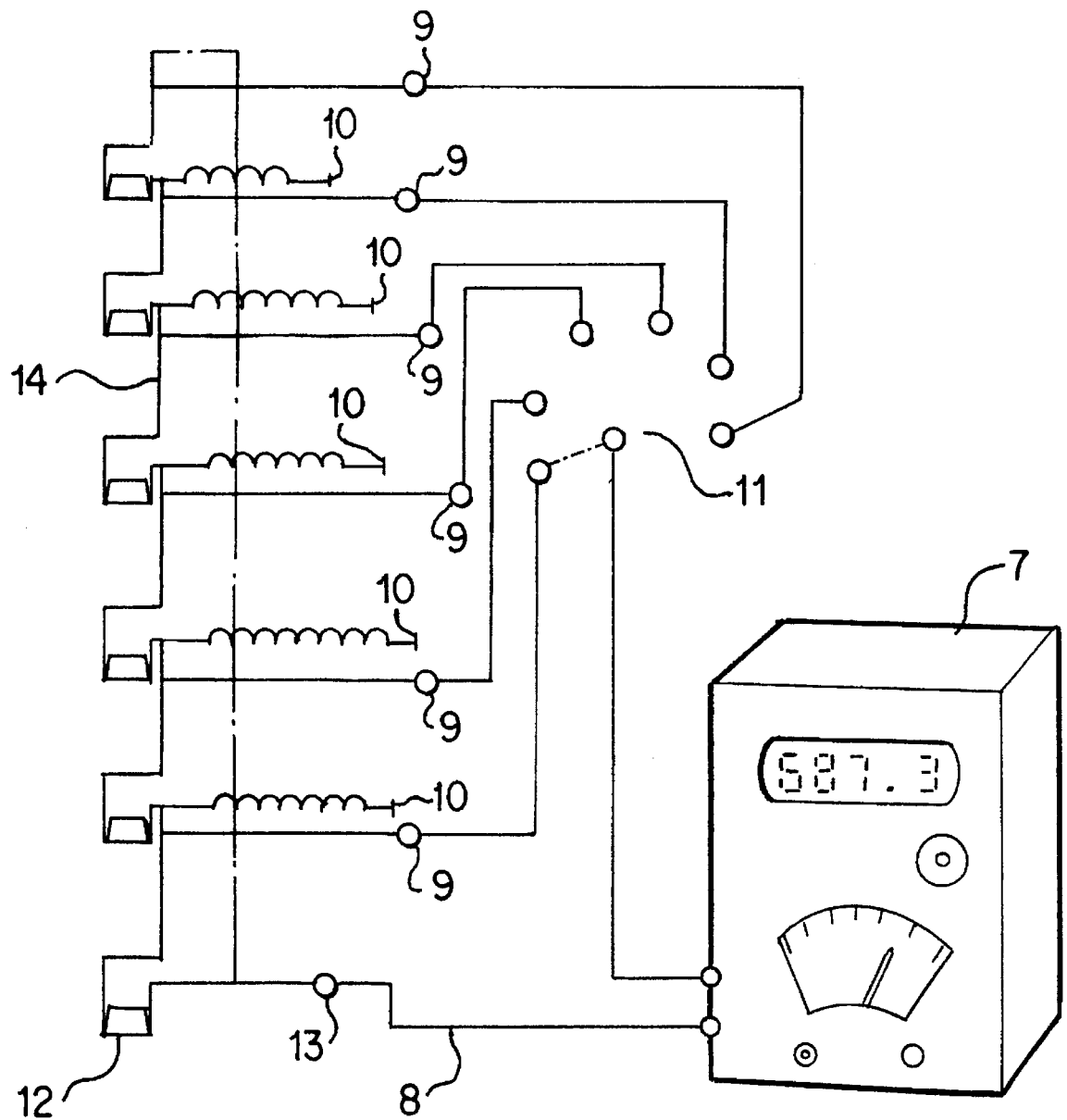
FIG. 2 is a schematic of a multi-chambered apparatus suitable for subjecting microorganisms to an EM fled.

A multi-chambered apparatus may be used to facilitate either multiple, simultaneous isolations, or to achieve a greater enrichment. Such a multi-chambered apparatus is illustrated in FIG. 2. With reference to FIG. 2, a source of EM field (7) is connected to common electrode (13) and to one of a plurality of variable electrodes (9) via a switch (11). All electrodes are immersed in a chamber (14) containing the culture medium and microbial mixture that is to be processed. In a preferred embodiment, the chamber will have one or more drain valves (12) at different positions in the chamber (14). The chamber will also preferably contain a plurality of flow valves (9) such that the flow of medium past a common electrode can be controlled. In the most preferred embodiment, the EM field source (7) is tunable, as described above.

EM radiation was thus used to encourage the replication of the desired species and to suppress replication of unwanted organisms. This technique was based on the observed behavior of microorganisms in response to EM radiation wherein particular organisms prosper under the influence of particular EM fields and are suppressed under EM fields of other parameters. The technique permits the isolation of microorganisms in a culture medium prepared from the same soil in which they live in the wild. Organisms so isolated exhibit no variation from those in the wild state.

All of the microbial strains used in TLB were isolated under specific EM field parameters. The method is fast and accurate. More importantly, it allows culturing without inducing variations from the original characteristics of the wild strains, since culture media having the same composition as the wild environment can be used. In soil, substances change form endlessly, organic compounds become inorganic compounds, and vice versa. Factors such as temperature, humidity, redox potential, etc. also change constantly.

Electromagnetic irradiation has also been used to solve the second problem incurred in manipulating natural isolates (i.e. the introduction of DNA into recipient cells). Such irradiation accomplished the electroporation of DNA. Methods and apparati for accomplishing such electroporation are described in CN patent applications 94103368.6 and 94103474.7, both herein incorporated by reference. Electroporation has proved to be an effective method of transferring DNA to a wide range of bacterial species (Trevors, J. T. et al., *Meth. Molec. Cell Biol.* 2:247–253 (1991); Chang, D. C. et al., In: *Guide to Electroporation and Electrofusion*, Academic Press, San Diego, (1992); Lin, L.S. et al., *Biotechnol. Tech.* 7:823–826 (1993); all herein incorporated by reference).

The use of EM to facilitate the introduction of DNA into a recipient strain has the substantial advantage that the DNA may be incorporated into a bacteriophage ("phage") vector (such as the bacteriophage lambda). It is generally asserted in the art that a bacteriophage is "specific" to its own host bacterium, and thus that a particular bacteriophage will only be able to infect its own host bacterium and reproduce by replication. Thus, for example, conventional recombinant methods would not allow the use of bacteriophage lambda to introduce DNA into a Streptomyces. In contrast, the use of EM permits the use of phage vectors in which neither the donor nor recipient of the transferred DNA is the natural host for the phage. The use of EM causes the bacteriophage to become capable of non-specific penetration into non-native host bacteria.

The first step in such a recombinational process is to select the DNA donor strain. The donor strain is then cultured and overexpressed in an appropriate liquid medium under EM radiation. When the bacteria count in the liquid medium reaches a certain minimum, the EM field parameters are changed to a condition which promotes rapid infection of the donor cells by preconditioned phages. A further change in field parameters stimulates accelerated replication of phage in the donor cells leading to cell lysis and yielding a bacteria-free phage lysate. The second step is the selection of a recipient strain. The recipient bacteria are then grown in liquid medium in a controlled EM field. When the cell titer reaches a desired level, the prepared phage solution is added, and the EM field parameters are changed to promote the phage infection of the recipient cells.

This method is based upon the observation that each microorganism has its own preferred, specific electromagnetic field. Since the components and molecular structures of different microorganism differ, they have different electronegativities. Each strain has a strong tendency to grow and reproduce in its preferred EM field; conversely, each strain can be suppressed by exposing them to unsuitable EM fields. This phenomenon permits the isolation of particular species electromagnetically.

B. The Component Strains of the TLB Fertilizer

As indicated, the TLB microbial fertilizer comprises four bacterial strains whose genetic makeups have been altered by a recombinant DNA technique—a nitrogen fixer, a phosphorus decomposer, a potassium decomposer, and a strain that decomposes carbon. The process of manipulating these strains includes phage lambda infection and lysis of the donor cells, infection of the recipient cells by the bacteriophages carrying the donor DNA, and integration of the recombinant DNA into the recipient cell's genome. All phases of the process are accomplished under the influence of controlled EM radiation of specific intensity and frequency.

A central feature of the TLB fertilizer is the fixation of atmospheric dinitrogen by a genetically engineered $N_2$-fixer bacterium. The expression of this ability in the TLB symbiotic community is enhanced by the assistance of the five other microorganisms. All the functions of the TLB fertilizer— $N_2$—fixation, P—, K—, and C-decomposition— depend on the mutual interaction of the six microorganisms. This interdependency can be described as follows:

The carbon nutrient required by the $N_2$-fixer bacterium in TLB is provided by the C-decomposers, which convert the complex organic compounds in coal, shale, oil, peat, etc. into simple compounds such as sugars, alcohols, and organic acids. The $N_2$-fixers obtain their necessary phosphorus from the metabolic activity of the P-decomposers which convert immobilized phosphorus (present as rock phosphate in the TLB) into available phosphorus nutrient. The potassium nutrient required by the $N_2$-fixers is provided by the K-decomposers which activate the potassium present in soil adjacent to the TLB granule.

The phosphorus decomposer bacterium needs nitrogen, which is supplied by the $N_2$-fixer. Its carbon requirement is supplied by the C-decomposers, which break the high molecular weight compounds in this material down into simple carbohydrates. Similarly, the P-decomposer's potassium requirement is provided by the K-decomposer bacteria.

The potassium decomposer's carbon needs are provided by the C-decomposers and its phosphorus requirement is satisfied by the by the P-decomposer.

In a similar manner, the potassium, phosphorus, and nitrogen needs of the carbon decomposer are satisfied by the K-decomposer, P-decomposer, and the $N_2$-fixer.

In sum, within the TLB fertilizer, all four strains live in a closed symbiotic community in which their metabolisms are closely interdependent.

Two yeast strains are used to enhance the output of the engineered bacteria. Besides carbon, hydrogen, phosphorus, potassium, sulfur, and various trace elements, a certain amount of growth factors, such as vitamin B complex, etc., is important for optimal bacterial growth. Thus, yeasts are incorporated into TLB in order to provide these factors. The $N_2$-fixing process requires large amounts of ATP; the amount of ATP naturally present is not enough to fuel biological $N_2$-fixation. Thus, in the most preferred embodiment, a yeast fermentation technique is used to compensate for any large energy deficit. During fermentation, in the respiratory process $CH_3COCOOH$ is formed. The mechanism is

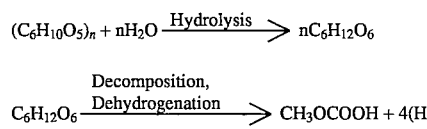

The $CH_3COCOOH$, together with the phosphorylation of the P produced by the P-decomposers, form ATP. This compound stores the energy released in the respiration cycle.

All of the preferred microbial strains of the TLB formulation were deposited on Jul. 11, 1994, with the American Type Culture Collection, 12301 Parklawn Drive, Rockville, Md., United States. The deposit was made under the terms of the Budapest Treaty governing microbial deposits. The deposited TLB fertilizer was found to be viable and was accorded ATCC Accession number ATCC 55597.

1. The Nitrogen Fixing Microorganism

Hundreds of species of more than 70 genera have been found to possess nitrogen-fixing ability and: many of these have been studied. Few, however, have been found in prior studies to be suitable for practical use. Many of these prior studies have found that $N_2$-fixer strains isolated on laboratory culture media show a fair nitrogen-fixing capacity under limited conditions but show much less or no activity in the field. The variations caused by the isolation procedure undoubtedly contribute to the loss of nitrogen-fixing ability by the wild Strains. Prior researchers have attempted to avoid variation by mimicking the growth conditions of the wild strains. However, no matter how subtly designed the artificial medium, it cannot reproduce natural conditions. The use of EM radiation, as described above overcomes this problem.

To boost their $N_2$-fixing efficiency and broaden their environmental adjustability the TLB technique uses a recombinant DNA technique to create new engineered strains. A free-living bacterium showing strong natural $N_2$-fixing power and good environmental adaptability was selected as the $N_2$-fixer gene (nif) donor. A saprophytic bacterium of the actinomyces group was chosen as the recipient organism because of its good adaptability. Recombination was accomplished under controlled EM radiation to produce a new, artificial strain. Some of the procedures involved in the process are complex and some of the mechanisms unclear. However, an understanding of the underlying mechanism is not needed to practice the invention.

The preferred nitrogen fixing bacterium ($GN_{02}$) is a genetically modified recombinant strain of *Streptomyces jingyangensis*. The bacterium was modified to contain the nifHDK nitrogen fixiation genes of an *Alcaligenes faecalis* strain that was isolated from the soil of Big Ha Farm near Qiqihaer City, Heilongjiang Province, PRC. In lieu of these strains, other suitable nitrogen-fixing strains can be used as either the donor or recipient of a nitrogen-fixation gene.

The *Alcaligenes faecalis* strain from which the preferred nitrogen-fixing gene was derived is normally found in soils of pH 5.5 to 8.5, but live optimally at soil pH 6.8–7.2. Three noteworthy features distinguish it from the other common free-living N-fixers: it tolerates a wide range of soil types, it tolerates a broad pH range with its strongest N-fixing efficiency at pH 6.8–7.2, and, perversely, when grown by the usual culture methods. It shows no N-fixing ability. The *Alcaligenes faecalis* strain is a free-living nitrifier, has a strong $N_2$-fixing ability, and has good adaptability relative to other reported free-living strains.

Preferably, EM irradiation is employed to produce the desired nitrogen fixing bacterium. The use of EM permits the cloning of a gene in a bacteriophage vector such as a lambda vector, and its subsequent introduction into a strain such as *Streptomyces jingyangensis* that is not a natural host for the bacteriophage.

2. The Carbon Decomposing Microorganism

The $GN_{02}$ strain fixes atmospheric nitrogen by its metabolic activity, the efficiency of which is determined by various factors, chief among which is nutrition. Of the required nutrients, the most important is carbon. The TLB method provides for a supply of carbon to assure the normal metabolism of $GN_{02}$ and the other symbiotic bacteria of the TLB fertilizer.

The most effective carbon sources for supporting the nitrogen fixing activity of $GN_{02}$ are glucose, saccharose, or soluble starch. These carbon sources are too expensive and available in too limited a supply for use in agricultural production. Thus, it is preferred to incorporate into the TLB fertilizer a microorganism that is capable of degrading more abundant and cheaper carbon sources into glucose or other compounds that can be assimilated by the $GN_{02}$ strain.

In particular, coal mine waste, weathered coal, oil-containing shale, peat, and similar fossil fuels or fuel byproducts or petroleum residues are the preferred carbon sources of the present invention.- These materials are abundant and inexpensive. Indeed, coal mine waste is itself a waste product, and hence, in one embodiment, the present invention can be used to alleviate the adverse environmental effects of coal mine waste.

It is usually thought that the weathering of coal or coal waste is caused by the action of wind and rain. More important, however, is the effect of the metabolic activity of several species of microorganisms. The organic polymeric compounds in weathered coal and waste are converted to simple sugars, alcohols, and organic acids by this metabolic pathway. But here, too, these organisms in their wild state are not suitable to be used directly in TLB fertilizer because their activity level is low and they have narrowly defined environmental requirements. A naturally occurring microorganism that was capable of such decomposition was therefore isolated and modified by recombinant means to produce a superior coal-waste decomposing strain.

The most preferred natural isolate was *Polyangium cellulosum*. These bacteria are capable of decomposing the high molecular weight compounds in weathered coal and coal waste to simple carbohydrates such as pentose, hexose, disaccharose, etc., producing a small amount of organic acids and alcohols in the process. This bacterium is widely distributed in weathered coal and coal waste. Other strains may be equivalently employed.

Although the genetic basis for the capacity of this strain to decompose coal and coal-waste is not fully known, such information is not needed in order to manipulate the strain. DNA can be obtained from the strain by EM-induced electroporation with phage lambda, and by the subsequent lysis of the strain. The DNA may then be used to transform a recipient bacteria and the transformants may be screened to identify clones that are capable of decomposing coal waste. A preferred recipient of such DNA is *Streptomyces jingyangensis*, although other strains may be equivalently employed.

3. The Phosphorus Decomposing Microorganism

The $GN_{02}$ bacterium requires a certain amount of phosphorus to fix nitrogen. The preferred source of phosphorus for this purpose is water-soluble phosphates, such as common laboratory salts. Such phosphate sources may be employed in accordance with the present invention. However, because such phosphates are quite expensive and in limited supply, it is preferred to employ lower cost phosphate sources in the fertilizer of the present invention.

Because the free sulfuric acid in calcium superphosphate was toxic to the microorganisms, this compound was also not suitable for use in the fertilizer. Diammonium phosphate and ammonium dihydrogen phosphate were found to contain a large number of quick-acting $NH_4^+$ groups which adversely affected nitrogen-fixing efficiency.

The most preferred phosphorus source material for use in the fertilizers of the present invention is ground phosphate rock. Phosphate rock is cheap and widely available. Unfortunately, the phosphorus in phosphate rock is immobilized, mainly as $Ca_{10}(PO_4)_6.(OH)_2$, $Ca_{10}(PO_4)_6.F_2$, $Ca_{10}(PO_4)_6.Cl_2$ and $Ca_3(PO_4)_6$. Since these phosphates are not water soluble, they must be decomposed into a soluble phosphate form in order to be taken up by the $GN_{02}$ bacteria.

This problem of solubilizing the phosphate of phosphorus rock is most preferably solved by incorporating a phosphorusdecomposer bacterium into the fertilizer. The phosphorus decomposer is able to convert the immobilized P to available water-soluble forms. A number of P-decomposer species have been discovered, but none in its wild state possesses the desired efficiency. For this reason a recombinant bacteria is preferably employed. The recombinant bacteria exhibits the ability to decompose rock phosphorus, and to grow well under soil conditions. The most preferred such recombinant bacterium is formed by transforming *Streptomyces jingyangensis* with DNA obtained from a natural isolate of *Bacillus megaterium phosphaticum*. Such a strain may be obtained from weathered phosphate rock, or from other similar sources.

4. The Potassium Decomposing Microorganism

The $GN_{02}$ N-fixer bacterium also requires potassium to sustain its metabolism. Most preferably, potassium is provided from water-soluble potassium salts. Such salts may be present in the soil sample that receives the fertilizer. In some cases, however, the soil supply of such salts is limited and does not provide the long-term effect required for the N-fixer bacterium. Thus, in a preferred embodiment, a K-decomposer bacterium is employed to decompose potassium from weathered potassium rock. In the most preferred embodiment, the K-decomposer is a recombinant bacterium formed by transforming *Streptomyces jingyangensis* with DNA from a potassium rock decomposer strain, *Bacillus mucilagneosus* var. Krassilnikov. Equivalent strains can, however, alternatively be employed.

5. The Yeast Growth Factor Producer

In following their metabolic pathways, the preferred microorganisms of the fertilizers of the present invention ($GN_{02}$ [the $N_2$-fixer], $PF_{02}$ [the P-decomposer], $KF_{02}$ [the K-decomposer], and $MF_{02}$ [the coal-decomposer]) require not only major nutrients (such as carbon), but also small amounts of growth factors such as thiamin, heptoflavin, nicotinamide, etc., and also certain trace elements. Most preferably, such factors are provided in the fertilizers of the present invention by incorporating a growth factor producing microbe into the fertilizer. In TLB, the most preferred embodiment of the invention, such growth factors are supplied by the metabolic activity of an artificially enhanced yeast included in the TLB microbial community. In the most preferred embodiment, the yeast will be a *Saccharomyces diastaticus* strain.

6. The Yeast Energy Producer

The TLB nitrogen-fixing process, which is an N-reduction process, requires energy. ATP functions in bacterial cells to balance exergonic and endergonic reactions. Thus, the oxidation of a high-energy molecule frees energy, a part of which is used to phosphorylate ADP or AMP and to thereby produce ATP. In this process, the chemical energy of certain compounds is stored in the high-energy phosphatic bond of ATP—from free energy to ATP. The process can be visualized as:

Carbohydrate→→free energy+ADP+Pi→→→→ATP

When the cell requires free energy, ATP can be hydrolyzed to ADP and Pi to generate a large amount of energy. ATP acts as the energy carrier. Both the energy release of ATP and the generation of ATP result from the phosphorylation process from high-energy to low-energy reactions. In TLB the mechanism is as follows:

1. Pyruvic acid reacts with phosphate ion to generate acetyl phosphate, protons, and CO2:

$CH_3.CO.COOH+Pi \rightarrow CHP3.CO-Pi+2(H^+)+CO_2$

2. Acetyl phosphate and ADP undergo phosphorylation to form ATP:

$CH3.CO-Pi+ADP \rightarrow ATP+CH_3.COOH$

3. The protons thus produced reduce oxidative ferrodoxin to a reductive ferrodoxin:

$Fd_{ox}+n(H+) \rightarrow Fd_{red}$

4. Nitrogenase activates gaseous nitrogen ($N_2$) to form the complex nitrogenase and nitrogen which is then reduced by the reductive ferrodoxin:

$Fd_{red}+N_{ase}+N_2.Nase_{red}+Fd_{ox}$

5. This reduced complex then accepts the ATP generated in step 2 and existing ATP to produce ammonia. The reaction repeats steps 1 through 5, constituting one cycle.

$N_2.Nase_{red}+nATP \rightarrow NH_3+nADP+nPi$

It is seen from this chemical pathway that the production of ATP is an important factor in N-fixation. Although this process has been noted in several recent studies of biological $N_2$ fixation, little effort has been made to use it. Rhizobium makes its ATP from the secretions of leguminous roots, and photosynthetic bacteria make ATP from solar energy. One of the main reasons that free-living N-fixers have such low N-fixing ability is the low level of ATP generated in these cells. Since the new genetically engineered strains possess a much higher N-fixing ability, they require more ATP. The production of ATP is controlled by the concentration of pyruvic acid and available phosphate produced by the P-decomposers and by the $O_2$ partial pressure. The TLB yeast generates pyruvic acid from the fermentation matrix thus increasing the pyruvic-acid concentration. This complex containing pyruvic acid constitutes the respiratory matrix for the TLB organisms. The products of the microorganisms's respiratory metabolism and the available phosphate generated by the P-decomposers make it possible to synthesize ATP by oxidative phosphorylation. The energy released by the oxidation of pyruvic acid is almost four times that released in the glycolytic pathway. The yeast used in TLB is an enhanced organism which produces pyruvic acid under controlled fermentation. The preferred yeast for this purpose is *Saccharomyces sinenses* Yue.

7. Provision of Trace Elements

The four principal microorganisms in TLB require the trace elements calcium, magnesium, sulfur, boron, manganese, zinc, molybdenum, iron, copper, sodium, and silicon. Commercially available reagents containing these elements may be used to supply these elements. More preferably, crude magnesium sulfate (content 70% >MgSO4 7H$_2$O $\geq$40%) and crude sodium sulfate (content 70% $\geq Na_2SO_4 \geq$40%) may be employed. Such crude compositions contain almost all of these trace elements and satisfy the requirements of the TLB microorganisms. These materials are therefore preferably included in the TLB matrix during manufacture.

II. The Preferred Fertilizer Formulation

The microbial strains of the present invention may be employed singly, or in combination. When used in combination, the microbes will most preferably be incorporated into a highly organized granule, termed "TLB". The TLB granule has three components. It is composed of a central granule surrounded by an intermediate layer, which, in turn is enclosed by an outer film or coating. The central granule contains rock phosphorus and the P-decomposing strain. The intermediate layer comprises all of the remaining microbial strains. The intermediate layer is coated with an external film that serves to adsorb much of the oxygen in the air passing into the granule. The external film serves to limit the diffusion of oxygen into the granule, to protect the nitrogen fixing microorganism from damage caused by oxygen, to protect the structural integrity of the inner layers, and to create a closed metabolic environment. The TLB fertilizer appears as small spherical granules (approximately 2–4 mm in diameter).

A. The Structure of the TLB Fertilizer

The TLB fertilizer serves several functions. First, it serves as a vehicle for applying the microorganisms to crops and plants. Second, it provides a means for delivering phosphorus, carbon, and potassium to the soil.

All the six microorganisms in TLB require phosphorus for their respiratory metabolism. However, phosphorus salts are highly labile and react quickly with various cations in soil to form water-insoluble compounds. In practice, the effective uptake ratio for chemical phosphate fertilizers is normally 10 to 25 percent and can sometimes be less than 10%. This occurs mainly because phosphates are easily immobilized in soil. Calcium, magnesium, iron, and aluminum cations present in soil react with phosphate ions to form compounds of low water solubility and thus unavailable to plants. Preventing direct contact between phosphate ions and these various cations is thus of major importance in designing the structure of the TLB granule. In the TLB fertilizer, therefore, the phosphate rock granule is located in the center of the granule, and is enclosed in a layer of coal waste or weathered coal dust which shields the phosphorus supply (phosphate rock with the phosphorus-decomposer bacteria) from contact with ambient soil.

The rock phosphate powder is slowly decomposed by the P-decomposer to release active phosphate ions which are readily used by the other microorganisms and by the fertilized plants. Plant rootlets can penetrate into the TLB granule and obtain the released P nutrient directly. This structural feature minimizes the immobilization of the phosphate ions by soil cations and thereby greatly improves the phosphorus uptake ratio in TLB. Test results show P uptake as high as 85–90% in TLB.

TLB's primary fertilizing power lies in biological N-fixation. Nitrifier bacteria very quickly lose their nitrogen-fixing ability in the presence of oxygen, and the process is irreversible. Rhizobium has a strong ability to fix nitrogen precisely because it has a very good defense against oxygen. Thus, it is most desirable to exclude oxygen from the fertilizer in order to maintain the $N_2$-fixing capacity of TLB fertilizer. However, the other five bacteria in TLB are aerobic or facultatively aerobic and require oxygen for their metabolisms. This problem is most preferably solved by incorporating into the fertilizer both a biological and physical barrier to oxygen presence. In manufacture, TLB is therefore formed by in three steps: (1) creation of the phosphate rock core; (2) enclosing the phosphate rock in an intermediate layer made of a special organic compound (weathered coal and fermented bran); and (3) coating the intermediate layer with a film membrane of about 100 µm thick. When air passes through the outer film to participate in the $N_2$-fixation process, some of the oxygen is adsorbed onto the film by redox reaction. The amount of oxygen penetrating into the granule is thus considerably reduced. This restriction, plus the use of oxygen by the aerobic bacteria in the granule, reduces the internal $pO_2$ partial pressure to a level that no longer interferes with nitrogen fixation.

A large number of suitable fertilizer formulations can be employed in accordance with the methods of the present invention. In a particularly preferred embodiment the granule will be composed of a core, an intermediate layer and an outer film. The core in such embodiment is composed of: 65–70 parts by weight of 200 mesh powdered rock phosphate (containing 25% or more phosphorus, calculated as $P_2O_5$); 28–32 parts by weight of fermented wheat bran; 28–32 parts by weight of bittern (containing 50% $Na_2SO_4 \cdot 10H_2O$ and 50% $Mg_2SO_4 \cdot 7H_2O$). The intermediate layer in such embodiment is composed of 65–70 parts by weight of weathered coal or coal-waste (weathering degree over 80%, burning loss over 35%); 15–18 parts by weight of fermented bran; 0.1–1 parts by weight of bittern (containing 50% $Na_2SO_4 \cdot 10H_2O$ and 50% $Mg_2SO_4 \cdot 7H_2O$); and 1.5–2 parts by weight of chalk soil or lime. The outer film in such embodiment is composed of 2–3 parts by weight of talc powder and 0.2–0.5 parts of bone glue.

The fertilizer of such an embodiment is formed by grinding rock phosphate containing nutrient compounds into fine powder, mixing it with fermented wheat bran, bittern (composed mostly of sodium sulfate and magnesium sulfate), and then forming it into a spherical granular core. Weathered coal or coal-mine waste is ground into a powder, and mixed with wheat bran, bittern, lime or chalk soil, and formed into a layer around the rock phosphate core. The granule is then sprayed or otherwise coated with an aqueous solution of powdered talc and bone glue to form a film layer, so as to create a granule with a three-layered structure. The purpose of incorporating rock phosphate into the core layer is to facilitate the biological decomposition of the phosphate rock and to prevent the phosphorus from reacting with metal cations of the ambient soil. The purpose of the intermediate layer is to facilitate the fixation of nitrogen. The main purpose of the bittern is to promote bacterial metabolism and plant photosynthesis. The purpose of the outer film is to limit the diffusion of oxygen into the granule, to protect the nitrogen fixing microorganism from damage caused by oxygen, to protect the structural integrity of the inner layers, and to create a closed metabolic environment.

B. The Preferred Method of Producing the TLB Fertilizer

Figure 3:
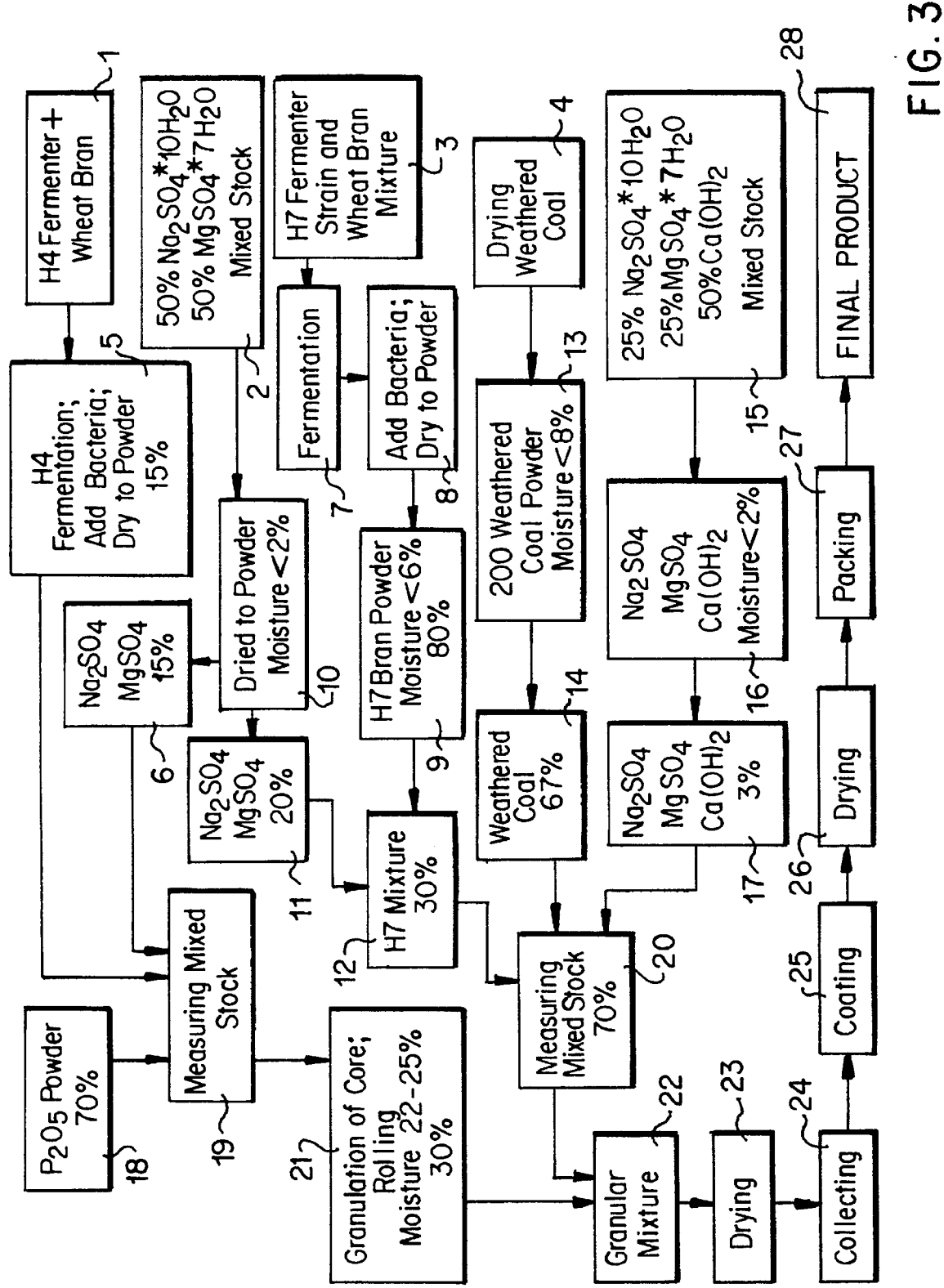
FIG. 3 is a schematic representation of the process steps of the preferred process for producing the TLB microbial fertilizer.

The preferred method of producing TLB is illustrated in FIG. 3. With reference to FIG. 3, wheat bran is fermented by the growth factor producing yeast (H4) (1). The bacteria are added to the wheat bran at a temperature of approximately 40°–50° C. The fermentation is conducted at a moisture content of 40–50%. P-decomposing bacteria are added and the mixture is dried to powder (5) having less than 6% moisture content. A 50%:50% mixture (2) of $Na_2SO_4 \cdot 10H_2O$ and $Mg_2SO_4 \cdot 7H_2O$ is dried to a powder (10) having a moisture content of less than or equal to 2% to form dried salts $Na_2SO_4$ and $Mg_2SO_4$ (6). The dried powder (5) and dried salts $Na_2SO_4$ and $Mg_2SO_4$ (6) are added together along with rock phosphorus powder having a moisture content of less than or equal to 2% (18) in a ratio of 15%:15%:70% to form a mixed stock (19). The mixed stock (19) having a wet moisture content of approximately 18% is granulated and rolled and conditioned to a moisture content of 22–25% (21).

Wheat bran is fermented (7) by the energy fermenting yeast strain (H7) (3). The fermentation matrix has a moisture content of 40–50%. The nitrogen fixing bacteria, the coal decomposing bacteria and the potassium decomposing bacteria are added to the fermentation and dried to a powder (8). The powder (8) is dried to a moisture content less than or equal to 6% (9). Dried salts (11) and the dried bran powder (9) are combined in a ratio of 20%:80% to form a mixture (12).

Weathered coal (4) is dried to a moisture content less than or equal to 8% and ground to a mesh 200 (13). A mixed stock (15) of 25% $Na_2SO_4 \cdot 10H_2O$; 25% $MgSO_4 \cdot 7H_2O$ and 50% $Ca(OH)_2$ is prepared. The mixed stock (15) is dried to a moisture content of less than or equal to 2%, and ground to a mesh 200 to form dried salt (16). The dried ground weathered coal (14) is combined with the mixture (12) and dried salts (17) in a ratio of 67%:30%:3% to thereby form mixed stock (20).

Granulated phosphate rock-containing mixed stock (21) is combined with mixed stock (20) in a ratio of 30%:70% to form a granular mixture (22) having a moisture content of 22–25%. The granular mixture (22) is dried to a moisture content of about 8% (23), collected (24), coated with a bone glue:water solution (1:7) containing talcum powder of greater than or equal to 200 mesh (25), and dried again (26). The material is then packed (27) to form the final product—the TLB fertilizer (28).

The above-described process may be carried out using appropriate manufacturing equipment. A preferred manufacturing equipment is shown in FIGS. 4A–4F.

Figure 4A:
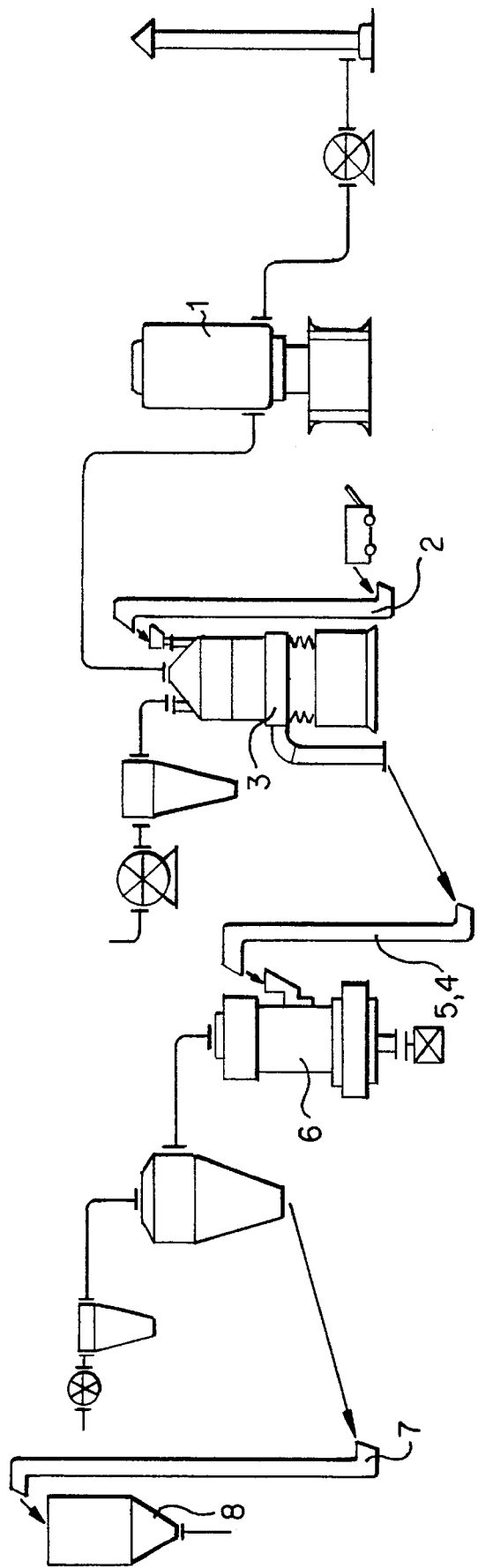

FIG. 4A shows the equipment used to prepare the weathered coal. With reference to FIG. 4A, a hot air generator (1) is used to dry weathered coal which is provided to a dryer (3) by a lift conveyor (2). The dried material is transported via a lift conveyor (4) to a mill (6) which grinds the material to suitable size. The milled material exits a filler (5), to a lift conveyor (7) which deposits the material into a stock tank (8).

FIG. 4B shows the equipment used to prepare the salts for the H4 stock tank. With reference to FIG. 4C, $MgSO_4$ and $NA_2SO_4$ are provided to a lift conveyor (9), which transports the material to a dryer (10). The dried material is then transported to a mill (12) which grinds the material to suitable size. The milled material exits a filler (11), to a lift conveyor (13) which deposits the material into a stock tank (61).

FIG. 4C shows the equipment used to prepare the salts for the H7 stock tank. With reference to FIG. 4C, $MgSO_4$, $NA_2SO_4$, and $Ca(OH)_2u$, are provided to a lift conveyor (9), which transports the material to a dryer (14). The dried material is then transported to a mill (15) which grinds the material to suitable size. The milled material exits a filler (11), to a lift conveyor (13) which deposits the material into a stock tank (62).

Figure 4D:
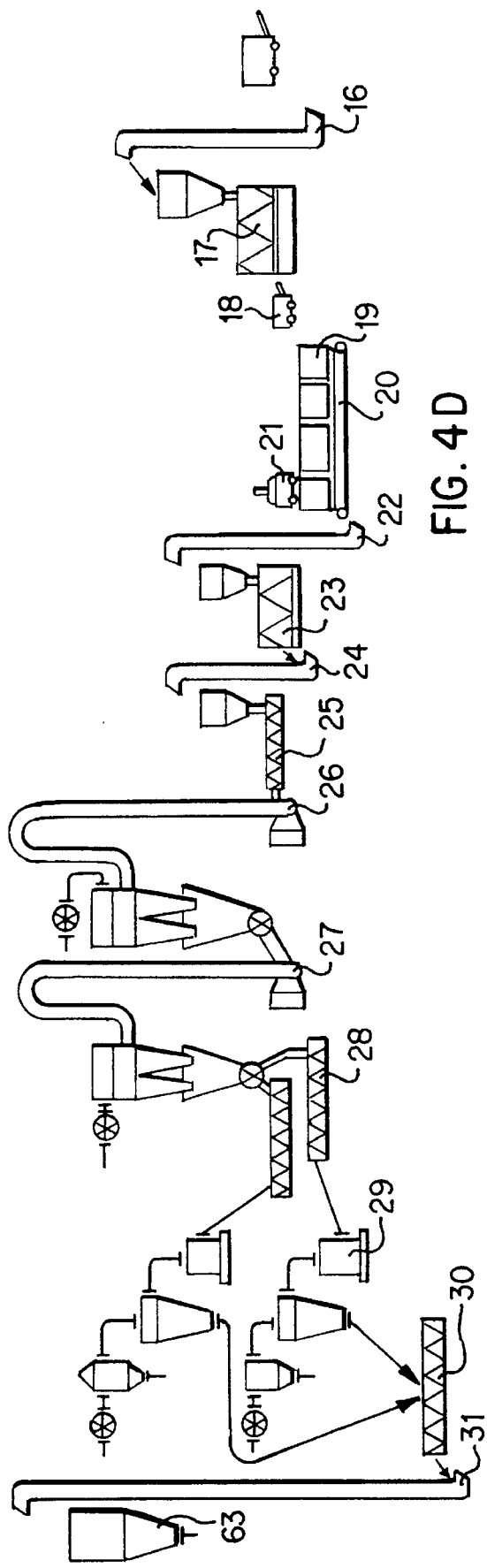

FIG. 4D shows the equipment used to prepare the H7 stock tank. With reference to FIG. 4D, wheat bran is transported via a lift conveyor (16) to a mixer (17) and heated to 40°–50° C. H7 yeast is then added, and the material is transported (18) to a fermentation pond (19), and then to a conveyor (20) to outlet equipment (21). The material is then transported via a lift conveyor (22) to a mixer (23) where the $N_2$-fixing bacterium, the coal waste decomposing bacterium, and the potassium decomposer bacteria are added. The mixture is transported via a lift conveyor (24) and a conveyor (25) to dryers (26, 27). The dried material is transported by conveyor (28) to crushers (29). The crushed material is transported by conveyor (30) to a lift conveyor (31), which deposits the material into a stock tank (63).

Figure 4E:
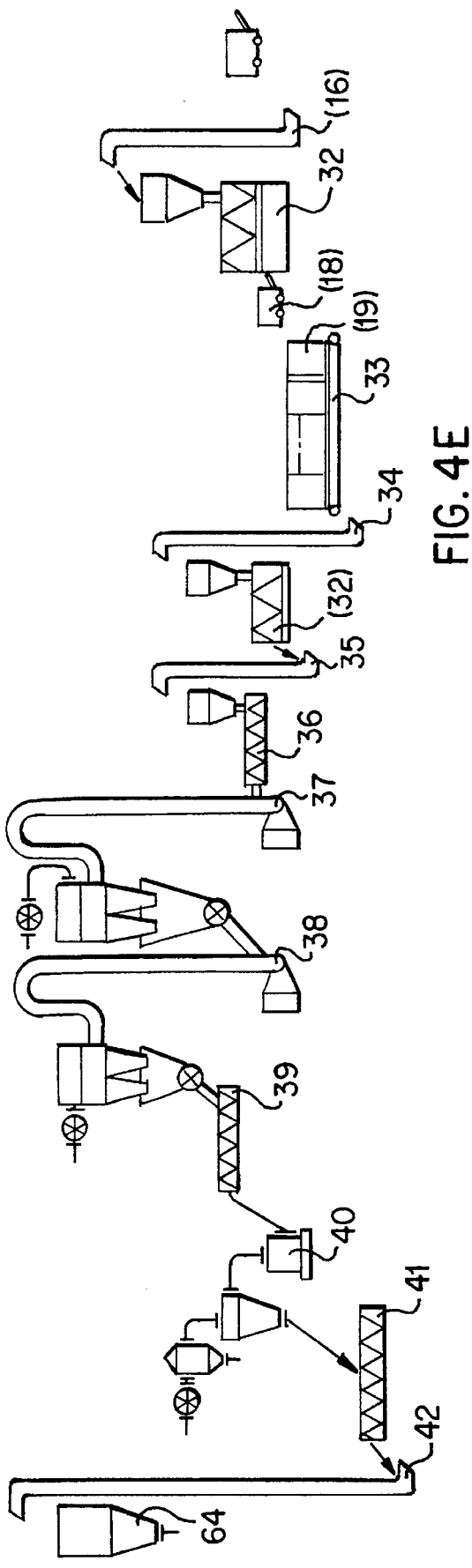
Figure 4F:
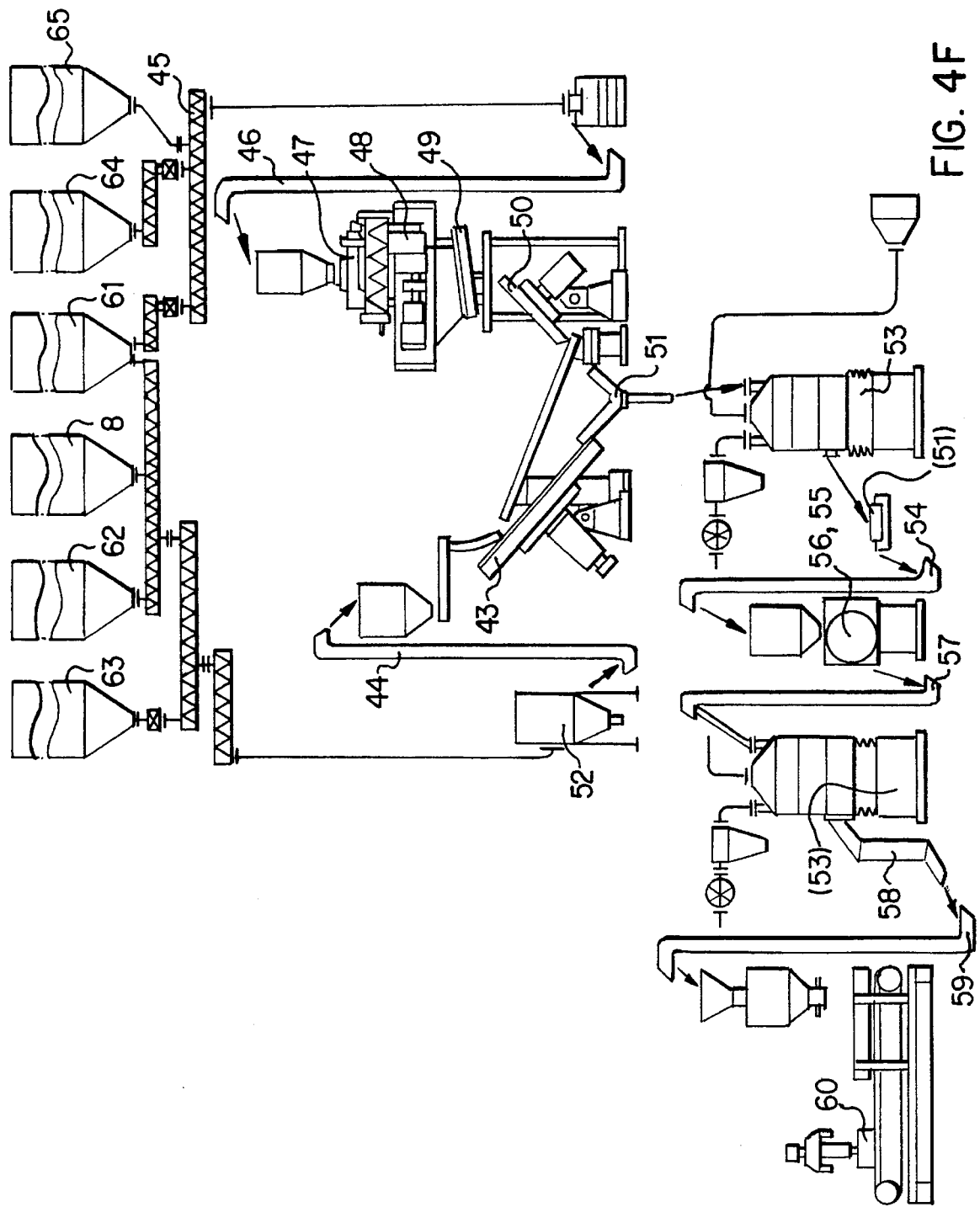

FIG. 4E shows the equipment used to prepare the H4 stock tank. With reference to FIG. 4E, wheat bran is transported via a lift conveyor (16) to a mixer (32) and heated to 40°–50° C. H4 yeast is then added, and the material is transported (18) to a fermentation pond (19), and then to a conveyor (33) to outlet equipment. The material is then transported via a lift conveyor (34) to a mixer (32) where the phosphorus decomposing bacterium is added. The mixture is transported via a lift conveyor (35) and a conveyor (36) to dryers (37, 38). The dried material is transported by conveyor (39) to crushers (40). The crushed material is transported by conveyor (41) to a lift conveyor (42), which deposits the material into a stock tank (64).

FIG. 4E shows the equipment used to finalize the production of the TLB granule. With reference to FIG. 4E, Material from the H4 stock tank (64) and the dried salts stock tank (61) are combined with powdered $P_2O_5$ (65) via conveyor means (45). The combined materials are transported to a mixer (47) via a lift conveyor (46). The material is scraped from the mixer (47) using a pressure scraper (48), and then sieved using a sieve shaker (49). The material is then granulated using a granulizer (50).

Still with reference to FIG. 4E, material from the H7 stock tank (63) is transported along with the dried salts of stock tank (62), with the weathered coal of stock tank (8) and the dried salts of stock tank (61) to a mixer (52). The mixed materials are then transported using a lift conveyor (44) to a granulizer (43). The granulated materials produced from the H4 granulizer (50) and the H7 granulizer (43) are conveyed by conveyor (51) to dryer (53). The dried material is conveyed (51) to a lift conveyor (54) which introduces the material into a coating apparatus (55). The coated granules are then sieved in a siever (56) and carried via a lift conveyor (57) to a dryer (53, 58). The dried granules are carried by a lift conveyor (59) to packaging equipment (60).

Although the preferred embodiment of the present invention contemplate a fertilizer that contains all four recombinant Streptomyces strains as well as the two yeast strains, it will be understood that alternative formulations are possible. Thus, if desired, the fertilizer may omit one or more of the above-described strains. For example, in phosphate rich soil, the fertilizer may be formulated to lack the phosphate decomposing bacterium. Alternate equivalent strains may be substituted in lieu of those described above.

The fertilizers of the present invention may be used in the same manner as conventional fertilizers. They may thus be applied to soil, by spreaders, sprayers, etc. Such application may be made once per year, or more frequently as desired.

Having now generally described the invention, the same will be more readily understood through reference to the following examples which are provided by way of illustration, and are not intended to be limiting of the present invention, unless specified.

EXAMPLE 1

Use of EM Fields To Isolate and Culture Microorganisms

The ability to isolate pure microbial cultures is very important both in scientific research and in industrial production. Isolating pure cultures means separating one strain of microorganism from its natural environment then growing it on an artificial culture medium. As indicated, two approaches to this problem have previously been attempted: (1) attempting to replicate microbes under the same conditions as their natural environment, and (2) determining what new conditions can be added to the common isolation culture media to make them more similar to natural conditions. Although a considerable number of microbial species has been isolated using such approaches, these constitute but a small fraction of the total number of microbial species.

As indicated above, one aspect of the present invention concerns a method for isolating and culturing microorganisms, which is characterized by placing natural material containing the desired microorganisms in a sterile container of suitable capacity, extracting the microorganisms in a solution of sterile water or liquid culture medium, isolating the desired microorganisms by applying an electromagnetic field of specific frequency and potential, and then obtaining a pure culture of the desired microorganisms by applying different electromagnetic field conditions. This invention can isolate and culture microorganisms rapidly and accurately with extremely small induced variation. Significantly, the isolated microorganisms retain their wild-state characteristics. The method is useful in microbial physiological and ecological research, natural ecological research, genetic engineering research, life sciences research, medical and pharmaceutical research, soil and fertilizer research and applications, pesticide and bacteriocide research and applications, and environmental pollution remediation. The advantages of the method include (1) the isolated microorganisms retain their wild-state characteristics with very little variation, (2) the isolation is rapid and the purity of the resulting cultures is high, (3) the process is simple, easy, and low cost, (4) the method can be applied to wild-type strains, and (5) it can produce pure microbial cultures which cannot be obtained by other methods. The following Procedures were used to isolated the above-described natural carbon-, potassium-, phosphate decomposers and the nitrogen fixing bacterium.

In all of the procedures presented below, an appropriate quantity of material containing the desired microorganism (soil, weathered minerals, natural organic residues, various biological products, etc. was placed in a container (such as that of FIG. 1 or 2) of appropriate capacity, an appropriate amount of liquid culture medium or sterile water was added, the mixture was allowed to stand for a certain time, and a suitable amount of the clear liquid was transferred to a sterile nonmetallic container. Electrodes were attached to each opposite side of the container, an electrical potential of a certain field density and amplitude at ambient temperature (normally 15°–36° C.) was applied. The desired strains were then isolated.

Procedure 1: Used to Isolate Alcaligenes species from a natural source

1. An appropriate amount of soil from the furrow slice horizon (i.e., from the top 35 cm of soil) was placed in a container of appropriate capacity, sterile water was added in the ratio of 30–80 ml water to one gram of fresh soil, stirred thoroughly, and allowed to stand at a temperature of 5°–36° C. for 6–24 hours.

2. An appropriate amount of clear filtrate was transferred to a sterile nonmetallic container and glucose or cane sugar was added in the ratio of 0.1–0.5 gram to 10–100 ml clear filtrate.

3. Electrodes were placed in each opposing side of the container. The electrodes were connected to a signal generator with a wavelength range of 1 µm–1.0 mm and the culture was subjected to an EM field having a wavelength of 40–100 µm and a peak EMF of 20–80 mv continuously for 2 to 10 hours.

4. While maintaining the EM field constant, the liquid was extracted from between the middle two electrodes. This liquid contained the desired nitrogen-fixer bacteria, for example, an Acaligenes species.

5. A liquid culture medium was prepared by stirring 1–5 grams of sugar into 20–100 mil sterile water, the bacteria-containing liquid separated under step 4 was added in the ratio of 5–50 ml bacterial liquid to 50–50 ml liquid culture medium, mixed thoroughly, and incubated under the conditions described under step 3 for 6–24 hours. This procedure produced a large quantity of the desired isolate bacterium.

Procedure 2: Isolation of a carbon-waste decomposer species from a natural source 1. An appropriate quantity of weathered coal or coal mine waste was placed in a container or appropriate capacity, sterile water was added in the ratio of 40–100 ml water to one gram of the carbonaceous material, stirred well and let stand at a temperature of 5°–36° C. for 6–24 hours.

2. An appropriate amount of clear filtrate was transferred to a sterile nonmetallic container and glucose or cane sugar was added in the ratio of 0.1–0.5 gram glucose or cane sugar to 10–100 ml filtrate.

3. A continuous EM field was created having a wavelength of 160–230 µm and voltage of 10–60 mV between any two electrodes in a multi-electrode insulated glass isolation chamber for 2–24 hours using a signal generator with wavelength range of 0.1 µm–1.0 mm (see FIG. 2).

4. While maintaining the EM field, liquid was extracted from between the middle two electrodes by a suitable means or by gravity flow. This liquid contained a pure culture of the desired coal-decomposer bacteria.

5. A liquid culture medium was prepared by stirring 0.5–5 grams of sugar into 20–100 ml sterile water, adding the bacteria-containing liquid separated under step 4 in the ratio of 5–50 ml bacterial liquid to 50–150 ml liquid culture medium, and mixing thoroughly. The culture was incubated under the conditions described under step 3 for 3–18 hours. This procedure produced a large quantity of the isolate carbon-decomposer bacterium.

Procedure 3: Isolation of a phosphate rock decomposer species from a natural source 1. An appropriate quantity of powdered, weathered rock phosphate was placed in a container of suitable capacity, sterile water was added in the ratio of 30–100 ml water to one gram of the powdered rock phosphate, stirred well and let stand at a temperature of 2°–36° C. for 6–36 hours.

2. An appropriate amount of clear filtrate was transferred to a sterile nonmetallic container and glucose and ammonium sulfate were added in the ratio of 0.1–0.5 gram glucose and 0.1–3.0 grams ammonium sulfate (or ammonium nitrate, urea, etc.) to 10–100 ml filtrate. 3. A continuous EM field was created having a wavelength of 10–60 µm and voltage of 10–30 mV between any single electrode pair or any two electrodes in a multi-electrode insulated glass isolation chamber for 2–16 hours using a signal generator with wavelength range of 0.1 µm–1.0 mm.

4. While maintaining the EM field constant, the liquid was extracted from between the middle two electrodes by a suitable means or by gravity flow. This liquid contained a pure culture of the desired phosphorus-decomposer bacteria.

5. A liquid culture medium was prepared by stirring 0.5–5 grams of glucose and 0.5–3.0 grams ammonium sulphate into 20–100 ml sterile water, adding the bacteria-containing liquid separated under step 4 in the ratio of 5–50 ml bacterial liquid to 50–200 ml liquid culture medium, and mixing thoroughly. The culture was incubated under the conditions described under step 3 for 3–30 hours. This procedure produced a large quantity of the isolate phosphorus-decomposer bacterium.

Procedure 4: Isolation of a rock potassium decomposer species from a natural source 1. An appropriate quantity of powdered, weathered potassium rock was placed in a container of suitable capacity, sterile water was added in the ratio of 30–100 ml water to one gram of the powdered potassium rock, stirred well and let stand at a temperature of 2°–36° C. for 6–36 hours.

2. An appropriate amount of clear filtrate from step 1 was transferred to a sterile nonmetallic container and glucose and ammonium sulfate were added in the ratio of 0.1–5.0 gram glucose and 0.1–3.0 grams ammonium sulfate (or ammonium nitrate, urea, etc.) to 10–100 ml filtrate.

3. A continuous EM field was created having a wavelength of 3–20 µm and voltage of 20–110 mV between any single electrode pair or any two electrodes in a multi-electrode insulated glass isolation chamber for 2–24 hours using a signal generator with wavelength range of 0.1 μm–1.0 mm.

4. While maintaining the EM field constant, the liquid was extracted from between the middle two electrodes by a suitable means or by gravity flow. This liquid contained a pure culture of the desired potassium-decomposer bacteria.

5. A liquid culture medium was prepared by stirring 0.5–5 grams of cane sugar and 0.5–3.0 grams ammonium sulphate into 20–100 ml sterile water, adding the bacteria-containing liquid separated under step 4 in the ratio of 5–50 ml bacterial liquid to 50–200 liquid culture medium, and mixing thoroughly. The culture was incubated under the conditions described under step 3 for 3–36 hours. This procedure produced a large quantity of the isolate potassium-decomposer bacterium.

EXAMPLE 2

Construction of the Nitrogen Fixing Bacteria of TLB

As indicated above, the $N_2$-fixing bacterium of TLB was produced by introducing a nitrogen fixing gene from an *Alcaligenes faecalis* strain into a *Steptomyces jingyangensis* isolate.

A. Isolation of the *Alcaligenes faecalis* Strain

The common methods of isolating $N_2$-fixer bacteria have many disadvantages. Soil is a complex material consisting of many inorganic and complex organic components that are constantly breaking down and interacting. Soil also contains a great many biologically active microorganisms, which compete actively for nutrients. When an isolation medium is designed for a specific purpose, it typically ignores many influencing factors. An example is the use of a non-nitrogen medium to isolate $N_2$-fixers. Although the resulting colonies are doubtless a pure N-fixer strain, it will have been inevitably modified by the artificial culturing conditions.

To avoid these disadvantages, electromagnetic fields were employed as described above, and the soil conditions were kept unchanged during the entire isolation and culturing process. All the microorganisms in the soil were simultaneously subjected to EM radiation; by regulating the frequency and intensity of the EM fields, the desired bacterial strain was isolated. The above-described deposited microorganisms obviate the need for others to isolate the bacteria from soil samples. The $GN_{01}$ strain was isolated from soil by the following procedure:

The culture medium employed was prepared by inoculating a soil sample of 150 g into culture medium that contained (per liter): 3.0 g $K_2HPO_4$; 3.0 g $KH_2PO_4$; 0.2 g $MgSO_4.7H_2O$; 0.2 g $Na_2SO_4.10H_2O$; 28 mg $Na_2MoO_{4+}.2H_2O$; 2.0 g yeast extract powder, 18 mg $FeSO_4.7H_2O$; 25 g glucose (or saccharose).

The two phosphate salts $K_2HPO_4$ and $KH_2PO_4$ were dissolved in 50 ml water (tap water acceptable) and sterilized. The remaining components were dissolved in exactly 600 ml water, then autoclaved.

A quantity of fresh soil was air dried and 300 g was placed in a 2 liter Erlenmeyer flask. Water was added to bring the total volume to exactly 2000 ml. The resulting solution was stirred well then let stand one day until precipitation was complete. The clear solution at the top of the flask was transferred by pipette to another Erlenmeyer flask. The final volume of the solution was 1200–1500 ml.

The autoclaved phosphate salt solution and the sterilized mixture containing the rest of the components were added together in a sterilized 2 liter beaker. After thorough stirring, the mixture was allowed to cool to about 50° C., at which point it was divided equally into three volumetric flasks. Soil solution was then added to bring the volume of each flask to 1000 ml and stirred well.

The content of each of the three volumetric flasks was divided equally into five 300 ml Erlenmeyer flasks (200 ml each). The flasks were cultured under shaking at 25°–27° C. for 72 hours. Growth of bacteria was observed in the flasks.

The cultured liquid media were then placed in a specially designed EM radiation chamber, where they were kept in a controlled EM field for 48 hours at 25°–27° C.

After locating the *Alcaligenes faecalis* strain in the EM radiation chamber, rubber plates were used to isolate the area from other parts of the chamber and the isolated medium removed. The culture medium isolated above was then reintroduced into the EM chamber and the above-described two steps were repeated. A very pure *Alcaligenes faecalis* strain was thus obtained by multiple isolation. The resulting *Alcaligenes faecalis* strain was designated $GN_{01}$, and was sealed and stored at approximately 0° C.

The $GN_{01}$ *Alcaligenes faecalis* strain is a short rod (0.6×1.0 μ). Older cells form fairly thick endospores. They produce a thin slime layer on saccharose media, more on beet sugar, and the most slime on glucose media. Each cell has four to six flagella, although older cells lack flagella. Under optimum conditions, it can fix 19 mg N per gram saccharose consumed, or 22 mg N per gram beet sugar consumed, or 25 mg N per gram glucose consumed.

The $GN_{01}$ can obtain its carbon requirements from a variety of materials: glucose, saccharose, starch, or any other material that can be utilized generally by saprophytic bacteria. It has the following biological characteristics:

(1) Its N-fixing activity is affected by Na ions as well as by Mo and Mg ions.

(2) It grows very rapidly on culture media containing certain quantities of growth factors such as flavin (B-2), thiamine (B-1), nicotinamide (B-5), etc.

(3) It is active within a temperature range of 5°–35° C., shows stronger activity at 18°–30° C., and strongest at 26±1° C. (i.e. at approximately 26° C.).

(4) The $GN_{01}$ is able to survive and grow in a relatively broad redox potential range: Eh=110 mV to 460 mV, optimum 180 mV to 320 mV.

(5) The $GN_{01}$ is also facultatively anaerobic and can live under a broad range of oxygen partial pressures. It generally grows under $pO_2$ pressures of 0.01–0.08, the optimum being 0.03.

(6) The G+C content of the DNA is 66 mol % (Tm method).

B. Isolation of the *Streptomyces jingyangensis* Isolate

The *Streptomyces jingyangensis* isolate was isolated in essentially the same manner as the above-described *Alcaligenes faecalis* strain.

At each soil collection site, the surface layer down to about 6 cm was removed, and a sample was then collected from the 6 cm–15 cm layer. 1–5 kg of soil was taken for each sample. The samples were then air dried and sealed against subsequent contamination.

Approximately 500 g of each soil sample was placed in a 2000 ml beaker and water added to being the total volume to 1500 ml. The mixture was stirred well and allowed to stand one day. The upper clear solution, about 100 ml, was then pipetted to another beaker, which was sealed and stored at a temperature below −1° C.

The culture medium contained (per liter of autoclaved soil solution) 25 g starch (wheat), 1.0 g $K_2HPO_4$; 2.0 g $MgSO_4 \cdot 7H_2O$, 2.0 g $Na_2SO_4 \cdot 10H_2O$; 0.01 g $FeSO_4$, and 0.5 g yeast extract powder.

The prepared culture medium was divided equally into 2 liter Erlenmeyer flasks and autoclaved. When the medium had cooled to about 50° C., 200 ml of soil solution was added to each flask and stirred well. The culture was then poured into a multilevel field isolation chamber for irradiation. After culturing for 72 hours at room temperature (about 20° C.) in the EM field, the desired recipient culture (designated $FS_{01}$) had been isolated.

After locating the FS01 growing area in the culture chamber, rubber plates were used to separate the culture from the medium in the adjacent areas. The $FS_{01}$ culture was then reintroduced into the EM chamber and the process repeated several times, from which FS01 strains of very high purity were obtained. They were sealed and stored at $<-1°$ C.

The $FS_{01}$ bacteria are generally quite similar physically under all conditions. Rod shaped, $0.3-0.5 \times 1.0-1.2$ μm. Young cells are short rods, while the old cellos are almost spherical. Old cells have no flagella and are non-motile. The G+C content of the strain was 68 mol % (Tm method).

The $FS_{01}$ strain is widely distributed in all kinds of soils, this strain grows well in soil solutions. The strain grows normally at temperatures from 5°–39° C. and at pH values from 5.0 to 9.0. Gram stain is not stable for this species; the organisms are Gram-variable. They grow normally on culture media containing trace amounts of quick-acting nitrogen. The bacterium becomes dormant in air-dried soil and revives in the presence of water C. Construction of the Recombinant Nitrogen-Fixing
Derivative of the *Streptomyces jingyangensis* Isolate The $GN_{01}$ strain can fix 25 mg N/g glucose under optimal conditions. This output is too low for wide-spread use in agriculture. Moreover, glucose is expensive, and the organism's N-fixing ability is further lowered by the effects of the complex soil environment encountered in the field. Thus, the $GN_{01}$ strain was not deemed to be suitable for use in biological nitrogen fixation-based fertilizers. Since the strain contained a desirable N-fixing gene, recombinant methods were employed to remove the gene from $GN_{01}$ and integrate it into the genome of the $FS_{01}$ recipient. The resulting hybrid strain possessed a high N-fixing ability and broad environmental adaptability.

A high efficiency nitrogen-fixing bacteria was produced by cloning a nitrogen fixation gene from the above-described *Alcaligenes faecalis* strain and introducing the cloned gene into the *Streptomyces jingyangensis* bacteria. For this purpose, a quantity of lysogenic temperate phage lambda, designated $A_{01}$, was inoculated into a liquid culture medium containing (per liter) 3.0 g $K_2HPO_4$, 3.0 g $KH_2PO_4$, 0.2 g $MgSO_4 \cdot 7H_2O$, 0.2 g $Na_2SO_4 \cdot 10H_2O$, 28 mg $Na_2MoO_4 \cdot 2H_2O$, 0.5 g yeast extract powder, 18.0 mg $FeSO_4 \cdot 7H_2O$, and 25.0 g glucose. The ingredients were autoclaved for 30 minutes. Growth was stopped when replication reached log phase, which in this case was $10^6$/ml.

Approximately 500 ml of the lysogenic culture was poured into a sterile square glass chamber then cultivated in an EM field. The EM field was then readjusted to optimum parameters as indicated above. An activating agent was added which initiated a large-scale replication of phage $A_{01}$ and modification of its DNA. After culturing for 240 minutes, the host cells lysed and the new temperate phage designated $A_{02}$ phage was released. $A_{02}$ thus obtained is capable of infecting the $GN_{01}$ bacterium, which becomes a lysogenic bacterium with specificity and can be replicated as such.

Although the $A_{02}$ phage is capable of infecting $GN_{01}$ cells under some conditions, the $GN_{01}$ still sees this DNA as foreign and its restriction system will suppress the phage DNA. This problem is alleviated using an EM field temporarily to deactivate the cellular restriction apparatus and to provide a suitable environment for replication of the $A_{02}$ phage in $GN_{01}$ cells. The method is based on the fact that enzymes show different activity under the influence of EM fields of varied parameters. The action of an enzyme can be thus enhanced or suppressed.

Infection was accomplished as follows. 100 ml of the liquid culture containing the $GN_{01}$ strain was inoculated into 500 ml of the same culture medium, which was mixed well and divided equally into 3 Erlenmeyer flasks. The flasks were cultured under constant shaking at approximately 26° C. for 9 hours. Growth was halted when the $GN_{01}$ count reached $10^6$/ml. The culture was sealed and stored at less than 0° C.

The resulting culture was transferred from the flask to a glass EM culture chamber and grown for 60 minutes under EM radiation to specific parameters as indicated above. After turning off the EM field, 60 ml of the $A_{02}$ phage culture and 1 g of "activator" were introduced simultaneously into the chamber. This mixture was cultured without radiation for 30 minutes at approximately 26° C., after which the EM field was again switched on for 6 hours. The "activator" used in the culture media of the present invention is most preferably β-hydroxybutyric acid. Alternatively, 3-indole-acetic acid ("IAA") may be used as the "activator" of the culture media described herein. The frequency and field potential were then readjusted and cultivation continued for another 10–15 hours. By this time, virtually all the $A_{02}$ phage had been absorbed into the $GN_{01}$ cells.

Next the culture was exposed to a suitable EM field, which led to large-scale replication of the $A_{02}$ in the $GN_{01}$ cells and their complete lysis. The phage thus released contained several DNA segments, including the desired nitrogen fixation genes (nifHDK).

Approximately 100 ml of the liquid $FS_{01}$ culture were inoculated into 500 ml of $FS_{01}$ culture medium and mixed well. The mixture was constantly shaken at approximately 26° C. for 8 hours. Growth was stopped when the $FS_{01}$ count reached $10^8$/ml.

The culture was then placed in a specially designed chamber and inserted between the electrodes of an electroporator, which was cycled on-off for 3 periods not exceeding 1 second each at 3–5 second intervals. Ambient temperature was kept between 2° and 5° C. During each on-cycle, three high-frequency high-voltage electron beams passed between the electrodes. The culture containing the porated $FS_{01}$ bacteria was quickly transferred to a special culture chamber and the above-described phage DNA was poured into the chamber at a ratio of 5 volumes of $FS_{01}$ cells to 2 volumes of phage. The chamber was then subjected to a specific EM field which suppressed the restriction nucleotidase activity of the $FS_{01}$ cells. This culture was grown at approximately 26° C. for 2 hours. The resulting culture was then further cultivated at the same temperature for 6 hours under an EM field suitable for replication of the recombinant DNA. The resultant strain was designated the $GN_{02}$, and comprised the preferred nitrogen fixing strain of the present invention.

D. Enrichment and Properties of the $GN_{02}$ Isolate

The isolation's of the $GN_{01}$ bacterium was accomplished as follows. Approximately 60 grams of fresh soil was placed in a large glass vessel to which was added 2400 ml water, which was thoroughly stirred and allowed to stand 48 hours. 1000 ml of the upper clear solution was transferred to a beaker.

The resulting solution was autoclaved for 30 minutes and stored at approximately 0° C.

The culture medium ingredients were mixed together as follows. To one liter of autoclaved soil solution was added 6.0 g $K_2HPO_4$, 2.0 g $KH_2PO_4$, 0.1 g $MgSO_4.7H_2O$, 0.1 g $Na_2SO_4.10H_2O$, 8.0 mg $FeSO_4.7H_2O$, 15.0 g starch, 10.0 g glucose and 20 g agar. The ingredients were autoclaved for 30 minutes.

When the temperature of the culture medium had cooled to 70°–80° C., 1.5 g of activator was stirred in and the mixture was poured into Petri dishes to make solid culture medium. After coagulation, 1 ml of the $GN_{02}$ culture was inoculated onto each Petri dish. The Petri dishes were then subjected to an EM field favorable to the metabolism of the $GN_{02}$ strain for 6 hours at approximately 26° C. The field was then switched off and the cultivation continued for 90 hours. Pure $GN_{02}$ colonies were thereby obtained.

A liquid culture medium was prepared from the same ingredients, except for the agar and the activator, and autoclaved. The sterile culture medium was allowed to cool to 70°–80° C., at which point the activator was stirred in thoroughly. Ten-twelve $GN_{02}$ colonies from the Petri dishes were inoculated into the liquid culture. This culture was exposed to the appropriate EM field for 6 hours at approximately 26° C., then the EM field was turned off and the cultivation was continued for another 72 hours. The result was a pure $GN_{02}$ culture. The resultant culture was sealed and stored at approximately 0° C.

E. Conditioning and Cultivation of the $GN_{02}$ Isolate

The $GN_{02}$ strain obtained from the above procedure possessed a much higher nitrogen-fixing activity level than the original $FS_{01}$ strain. To further improve the ability of the strain to adapt to the conditions in soil, the strain was conditioned in the following manner.

A culture medium containing the following components (per liter) was produced: 700 ml of autoclaved soil solution, 25 g saccharose, 0.8 g yeast extract powder, 4.6 g $K_2HPO_4$, 6.0 g $KH_2PO_4$, 0.3 g $MgSO_4.7H_2O$, 0.3 g $Na_2SO.10H_2O$, 20.0 mg $FeSO_4.7H2O$, 30.0 mg $Na_2MoSO_4.7H_2O$.

The culture medium ingredients were mixed and autoclaved. The activator (300 mg) was added when the medium had cooled to 70°–80° C. The solution was stirred well and divided equally into sterile Erlenmeyer flasks, about 200 ml each. Twenty-fifty ml of the $GN_{02}$ culture was then inoculated into each flask.

The flasks were shaken for 12 hours, during which period at each 2-hour interval the temperature was changed over the range 5°–40° C. in 5° increments. After such incubations, 1 ml of adjusting agent was added to each flask. The culture was then grown for another 30 minutes at 26° C. under a specific $GN_{02}$ EM field. The resulting strain possessed wide temperature adaptability.

After such adaptation to temperature, the resultant culture was adapted to various soil types and soil conditions. This was accomplished by placing 50 g of air-dried fresh soil into a vessel of suitable size and then adding 3–5 liters of water and stirring well. The mixture was let stand 2 hours after which the clear upper solution, or a filtrate of the mixture, was poured into 500 ml Erlenmeyer flasks.

Immediately after the temperature adaptation cultivation of the $GN_{02}$ bacteria was completed, 50–100 ml of that solution was placed in the initial fresh soil solution. The flasks were shaken for 60 hours, during which time the temperature was varied from 5° to 40° C. in 5° increments every hour. The culture was then grown under the specific $GN_{02}$ EM field for another 20 minutes at approximately 26° C. The final $GN_{02}$ culture had a count of $10^4$/ml to $10^6$/ml. $GN_{02}$ bacteria conditioned by this procedure were then suitable for use. The $GN_{02}$ strain contains 21 integrated copies of the *Alcaligenes faecalis* nifHDK genes.

As indicated above, TLB containing the $GN_{02}$ strain was deposited with the American Type Culture Collection.

EXAMPLE 3

Construction of the Carbon Decomposing Strain of TLB

Since $GN_{02}$ cannot degrade the complex carbon polymers in such substances, a recombinant microorganism that was capable of such decomposition was constructed. The carbon decomposing bacteria was produced by isolating a coal-waste decomposing bacteria, and then using recombinant DNA techniques to transfer DNA from that organism into a recipient *Streptomyces jingyangensis*, and acclimating the modified host to the environment.

A. Culturing of the Natural Coal-Waste Decomposing Bacterium

A natural isolate of *Polyangium cellulosum* was selected as the donor of DNA encoding the enzymes needed to decompose coal-waste. These bacteria are capable of decomposing the high molecular weight compounds in weathered coal and waste to simple carbohydrates such as pentose, hexose, disaccharose, etc., producing a small amount of organic acids and alcohols in the process. This bacterium is widely distributed in weathered coal and coal waste.

The *Polyangium cellulosum* cells were was isolated using the following procedure. Approximately 100 g of ground, air-dried weathered coal or coal waste was placed in a beaker and 300 ml water added and mixed. After standing 4–6 hours, the upper clear solution was transferred to the specially designed EM isolation chamber. The following culture medium was employed: 30 g weathered coal or waste ground to 180 mesh and air-dried; 1500 ml autoclaved soil solution; 2 g $MgSO_4.7H_2O$; 2.0 g $Na_2SO4.1OH_2O$; 2 g milk powder; 0.5 g yeast extract powder; 1.0 g activator. The culture was subjected to an EM field of optimum frequency and intensity at 28±1° C. for 64 hours, after which the desired bacteria had been isolated. The technique was the same as that applied to isolate the N-fixing bacteria, the only difference being the EM field parameters. The culture was then purified by repeating the above isolation step three times. After purification, the culture was sealed and stored under sterile conditions at 0±1° C.

The cells of *Polyangium cellulosum* were found to be rod shaped, 0.6–1.01 μm by 1.0–1.6 μm. Young cells are peritrichous while mature cells have flagella on only one side. Old cells have no flagella. This bacterium can form spores and can remain dormant for long periods in dry conditions. The colonies displayed small, regular cracks at the edges. Colonies were transparent colloids that become light gray over time.

Facultatively anaerobic, it shows relatively strong activity at oxygen partial pressure $pO_2$=1.02–0.04. The normal temperature range of the bacterium is 6°–35° C. When cultured outside of this range, the cells age and become dormant. They revive, however, when moisture and temperature are suitable. The optimum temperature range for the bacterium is 16°–25° C., within which there was no significant difference in growth. The cells were killed by exposure, in liquid media, to 65° C. When cultured on solid medium, the cells could survive to 76° C. The spores were killed by exposure to 85° C.

The bacterium has a strict water requirement: its highest activity occurs when the water content of powdered coal or waste is 20–36%, however, it shows some activity when water content is 37–70%. The strain exhibits only minimal activity at water contents below 12%. G+C=52 mol % (Tm). This bacterium was designated $MF_{01}$.

After isolation, an enrichment procedure was followed in order to condition the cells for artificial medium. The above-described culture medium was employed. The mixture, except for the activator, was autoclaved for 30 minutes. When the medium had cooled to 70°–80° C., the activator was stirred in. When the temperature had dropped to below 40° C., 100 ml of the purified culture was stirred in. The mixture was placed in the EM radiation chamber and grown for 3 hours under the EM field parameters appropriate for this bacterium, as indicated above. The EM field was turned off and the culture continued for another 72 hours. The concentration of bacteria in the final culture was $10^6$–$10^8$ cells/ml. The resulting culture was used as the donor of coal-waste decomposition genes. The culture was stored at 0±1° C.

B. Construction of a Carbon Decomposing Derivative of *Streptomyces jingyangensis*

The isolate used as the recipient of DNA from *Polyangium cellulosum* was *Streptomyces jingyangensis*. The *Streptomyces jingyangensis* was cultured on the following medium: 20.0 g wheat bran ground to 200 mesh, 1.5 g $K_2HPO_4$, 6.0 g $KH_2PO_4$, 2.0 g $MgSO_4.7H_2O$, 1.0 g $Na_2SO_4.10H_2O$, 0.01 g $FeSO_4.7H_2O$, 1.0 g activator, 1000 ml water. The above ingredients, except for the activator, were mixed in their given proportions, stirred well, and autoclaved for 30 minutes. When cooled to 70°–80° C., the activator was added. The resulting medium was then poured into four 250 ml Erlenmeyer flasks. This isolate was designated $FS_{02}$.

When the medium had cooled to below 40° C., 50 ml of the $FS_{02}$ strain was added to each flask. The flasks were cultured in the $FS_{02}$ specific EM field at about 27° C. for 2 hours. The EM field was switched off and the flasks were kept under constant shaking for 72 hours. A pure $FS_{02}$ strain was thus obtained with a count of 106–107 /ml. The culture was stored under sterile condition at 0±1° C.

Temperate bacteriophage lambda ($B_{02}$) was inoculated into a liquid culture of the $MF_{01}$ strain and cultivated at 26±1° C. for 6 hours. Approximately 500 ml of the resulting culture was placed in a sterile square culture chamber, which was placed in the EM radiation apparatus and grown for 60 minutes at 27° C. in a specific EM field. The EM apparatus was then reset to the condition that stimulates the replication of $B_{02}$ phage, which also causes its DNA to undergo recombination. After 4 hours, the host cells ruptured and the $B_2$ phage was released.

Approximately 150 ml of the MF01 liquid culture medium (1000 ml autoclaved soil solution; 4.0 g $MgSO_4.7H_2O$; 4.0 g $Na_2SO_4.10H_2O$; 1.0 g yeast extract powder; 3.6 ml activator; all ingredients, except the activator, were mixed well and autoclaved. As the mixture cooled to about 50° C., the activator was stirred in thoroughly) was inoculated into 500 ml of the special $MF_{01}$ culture medium and stirred well. The resulting solution was divided equally into three 300 ml Erlenmeyer flasks and cultured under shaking at 27±1° C. for 12 hours. Growth was stopped when the $MF_{01}$ count reached $10^8$/ml and the culture was sealed and stored at 0±1° C.

Subsequently, the culture was placed in the special EM culture chamber and subjected to an EM field of controlled parameters for 90 minutes, see above. The field was switched off and 30 ml of the $B_{02}$ phage culture and 1 g of activator were simultaneously stirred into the chamber. This mixture was allowed to stand to 20 minutes. The resulting culture was grown under a specific EM field for 9 hours. The field parameters were then readjusted and the culture continued for another 9 hours. At this stage, almost all of the $B_{02}$ phage DNA had been absorbed into the $MF_{01}$ cells. The EM field parameters were readjusted to the condition that stimulates the replication of $B_{02}$ phage in the $MF_{01}$ cells. This led to lysis of the $MF_{01}$ cells and the release of large amounts of $B_2$ phage containing the desired genes. The resulting $B_{02}$ phage solution was sealed and stored at 0±1° C.

50 ml of the liquid culture containing the $FS_{02}$ strain was stirred into 4 Erlenmeyer flasks. The medium employed contained 10 g weathered coal ground to 200 mesh, 1000 ml $FS_{02}$ soil solution, 1.2 g yeast extract powder, 1.0 g $K_2HPO_4$, 12.0 g $MgSO_4.7H_2O$, 12.0 g $Na_2SO_4.10H_2O$, 0.01 g $FeSO_4.7H_2O$, 0.4 g NaCl, 1.0 g activator. All of the media ingredients, except for the activator, were mixed, autoclaved for 30 minutes and then cooled to 70° C. Activator was then added, and the culture medium was then divided equally among the flasks.

The culture was cultivated for 3 hours at the specific temperature for the $FS_{02}$ strain, by the end of which the $FS_{02}$ concentration was $10^6$/ml. The resulting $FS_2$ culture was then transferred to the specially designed chamber of the electroporator. At the appropriate frequency and potential, the electroporator was cycled on/off three times to pierce the cell walls. The interval was less than 6 seconds. This process was carried out at 3° C.

Approximately 30 ml of the $B_{02}$ phage solution was added to the $FS_{02}$ culture simultaneously with 1 ml of activator. The temperature was gradually raised to about 25° C. over 3 hours. The culture was then grown at this temperature for 60 minutes in an EM field at the appropriate frequency and potential. This alteration of the environmental condition repressed and killed the undesired DNA and permitted survival of the desired DNA. Finally, cultivation was continued under the new EM field parameters for an additional 3 hours, which stimulated the integration of the desired DNA into the $FS_{02}$ genome. By this stage, the genetic recombination was basically completed. The resulting culture was sealed and stored at 0±1° C.

The new bacterium obtained by the foregoing procedure was designated the $MF_{02}$ strain and possessed improved ability to decompose weathered coal and coal waste.

The $MF_{02}$ strain was adapted to temperature variation by culturing the strain in medium containing 1000 ml of autoclaved coal (or coal-waste) solution, 15 g saccharose, 0.5 g yeast extract powder, 0.3 g $Na_2SO_4.10H_2O$, 0.3 g $MgSO_4.7H_2O$, 300 g activator. All of the media ingredients, except for the activator (which was added after the mixture had cooled to approximately 70° C.), were mixed and autoclaved for 30 minutes then divided equally among several flasks. 20–50 ml of the $MF_{02}$ liquid culture was stirred into each flask, and the flasks were then shaken continuously for 12 hours. During growth, the temperature was varied over a 5°–40° C. range in increments of 5° C. every 90 minutes. At the end of 12 hours, 1 ml of an adjusting agent was added and the culture was grown in an EM field appropriate to the $MF_{02}$ for 60 minutes at 26±1° C.

The $MF_{02}$ strain produced by this conditioning process displayed good adaptability to a broad range of temperatures.

The $MF_{02}$ strain was adapted to different soil conditions by placing 500 g of fresh air-dried soil in a container, to which 2000–3000 ml water was added with stirring. The mixture was allowed to stand for 2 hours at room temperature, after which the clear solution was pipetted into 500 ml Erlenmeyer flasks.

As soon as the temperature adaptation of the $MF_{02}$ culture had been completed, 100–150 ml of that culture was immediately added to Erlenmeyer flasks containing about 500 ml of the fresh soil solution. These flasks were then shaken continuously for about 48 hours. The culture was then grown for another 40 minutes at $27\pm1°$ C. under the EM field appropriate to the $MF_{02}$ strain. After completion of this procedure, the concentration of the $MF_{02}$ strain reached about $10^7$/ml and possessed very good soil-type adaptability. The final culture was stored at 0±1° C. for later use in the preparation of TLB fertilizer.

$MF_{02}$ bacteria conditioned by this procedure were then suitable for use. The $MF_{02}$ strain contains 15 integrated copies of the *Polyangium cellulosum* carbon-decomposing genes.

As indicated above, TLB containing the $MF_{02}$ strain was deposited with the American Type Culture Collection.

EXAMPLE 4

Construction of the Phosphorus Decomposing Bacteria of TLB

The $GN_{02}$ bacterium requires a certain amount of phosphorus to fix nitrogen. In order to address this requirement, a recombinant bacteria was produced that had the ability to solubilize (i.e. decompose) the phosphorus contained in rock phosphorus. The bacterium was constructed by transforming a *Streptomyces jingyangensis* isolate with DNA obtained from a natural isolate of *Bacillus megaterium phosphaticum*. The Bacillus isolate was obtained from a sample of weathered phosphate rock.

*Bacillus megaterium phosphaticum* is widely distributed in weathered phosphate rock fines around phosphate mines. The bacterium can use a large variety of organic substances such as saccharose, lactose, and gelatin as its carbon source. Simple carbohydrates are the preferred nutrient source. The strain is chemoheterotrophic and facultatively anaerobic. At the end of its oxidative metabolic chain, the bacterium uses molecular oxygen as the electron acceptor. During metabolism, the bacteria secrete a thick slime layer, which decomposes the immobilized P to water-soluble forms. The chemical makeup of the slime layer is not clearly understood at the present time, but it is certain that no organic acids are generated in the bacteria's metabolism and that decomposition of the phosphate rock is not accomplished by acidolysis. The G+C content of the cells is 46 mol % (Tm).

A. Culturing of the Natural Phosphorus Decomposing Bacterium

To isolate the bacterium, a sample of weathered phosphate rock was pulverized to about 200 mesh, and added to a sterilized culture medium containing 8.0 g saccharose, 10 g ground weathered phosphate rock, 4.0 g $MgSO_4.7H_2O$, 4.0 g $Na_2SO_4.10H_2O$, 0.2 g $K_2SO_4$, 1.0 g yeast extract powder, 3.0 g humus, 1.2 ml activator, per liter of water. The culture medium was prepared without activator and autoclaved for 40 minutes. The activator and phosphate rock were added to the medium after the medium had been cooled to 70° C.

The culture was grown for 72 hours at 25°–28° C. It was then placed in the special EM radiation chamber and grown for 5–6 days under the EM field parameters appropriate to P-decomposers, as indicated above. The procedure succeeded in isolating a strain (designated $PF_{01}$) of *Bacillus megaterium phosphaticum*. The $PF_{01}$ strain was isolated in the target zone of the EM chamber. The culture thus obtained was inoculated into more of the same culture medium and grown for another 72 hours at 25°–28° C. The final bacteria concentration in the medium was $10^6$/ml. The culture was sealed and stored at −2° C.

The $PF_{01}$ isolate was found to be rod shaped, 0.5–0.7×1.2–1.8 μm in size. The cells were peritrichous and motile, and were found to be Gram-variable. The cells of the isolate could form spores on starch culture medium. Under dry conditions the cells became dormant but revived when conditions again become suitable.

B. Construction of a Phosphorus Decomposing Derivative of *Streptomyces jingyangensis*

The isolate used as the recipient of DNA from *Bacillus megaterium phosphaticum* was *Streptomyces jingyangensis*. The recipient bacterium was designated $FS_{03}$.

Temperate bacteriophage lambda ($C_{01}$) was inoculated into a liquid culture of the $PF_{01}$ strain and cultivated at 27°±1°C. for 18 hours under EM field parameters suitable for the replication of the $C_{01}$ phage's host cells. Growth was stopped when the concentration of $C_{01}$ lysogenic bacteria reached $10^6$ cells/ml.

Approximately 500 ml of the culture was then placed in the incubation chamber of the EM irradiation apparatus. The EM field parameters were then readjusted to stimulate the replication of the $C_{01}$ phage DNA in the host cells and their ultimate lysis. This cultivation continued for about 18 hours. After lysis, a large amount of modified $C_{01}$ phage was present. This preparation of lambda phage was designated phage $C_{02}$. This procedure enables the $C_{02}$ phage to infect the $PF_{01}$ bacteria under certain conditions, facilitates their replication, and renders them lysogenic.

The $C_{02}$ phage were adapted to the $PF_{01}$ host in the following manner. $PF_{01}$ cells were cultured in 250 ml of medium containing (per liter) 10 g ground weathered phosphate rock, 1000 ml soil solution, 5.0 g saccharose, 15.0 g starch, 2.0 g $MgSO_4.7H_2O$, 2.0 g $Na_2SO_4.10H_2O$, 1.0 g activator. Prior to inoculation, all of the media ingredients, except for the activator, had been mixed, autoclaved for 30 minutes and then cooled to 70° C. After the activator had been added, and medium was then divided equally among several 500 ml Erlenmeyer flasks. The flasks were shaken continuously for 8 hours at about 27° C. At the end of the 8 hours, the flasks were placed in an EM field specific to the PF strain and the culture was grown for another 6 hours. At the end of the 6-hour growth period, 20–30 ml of the phage culture and one gram of activator were added to each flask. The resulting mixtures were let stand for 3 hours at about 27° C.

At the end of the 3-hour resting period, the flasks were placed in the EM field and grown for another 4 hours, at which time almost all the $PF_{01}$ cells had been infected by the $C_{02}$ phage.

The EM field parameters were changed and the culture was exposed briefly for 10–15 minutes. The EM field parameters were then reset to the values initially employed. The culture was grown under this condition until almost all the $PF_{01}$ cells had been lysed by the $C_{02}$ phage. The resulting $C_{02}$ culture was sealed and stored at 0±1° C.

The recipient $FS_{03}$ bacterium was infected with the $C_{02}$ phage as follows. Approximately 50 ml of the $FS_{03}$ culture was inoculated into each of several 500 ml Erlenmeyer flasks that contained 250 ml of medium containing (per liter): 10.0 g ground weathered phosphate rock, 1000 ml soil solution, 1.0 g yeast extract, 5.0 g saccharose, 10 g starch, 2.0 g $MgSO_4.7H_2O$, 2.0 g $Na_2SO_4.10H_2O$, 0.01 g $FeSO_4$, 1.0 ml activator. The culture medium ingredients except for the activator were mixed well and autoclaved for 30 minutes. The sterile medium was then cooled to 70° C. and the activator was added.

The flasks were incubated for 8 hours at about 27° C. in an EM field specific to the $FS_{03}$ bacterium. The $FS_{03}$ concentration reached $10^8$ cells/ml. The flasks were then placed in the special cultivation chamber of the electroporator, which was set at a certain frequency and potential and cycled on-off three times. Each time interval should be less than 6 seconds. During this operation, the temperature was maintained at 3° C.

Immediately thereafter, 30 ml of the $C_{02}$ phage culture was added to each flask followed by 1 ml of activator. The temperature of the culture medium was allowed to rise gradually over 5 hours to about 27° C. The flasks were then incubated for 120 minutes at the same temperature under EM radiation at specific parameters, as indicated above. This EM field stimulated the replication of the desired P-decomposer DNA and suppressed replication of other DNA. Only the desired transformants survived. The EM field parameters were then changed and the culture was grown under this new condition for another 3-4 hours. The new EM field stimulated the transduction of the operative DNA and its recombination in the $FS_{03}$ cells. The resulting new recombinant strain was designated $PF_{02}$. The $PF_{02}$ culture was sealed and stored at 0±1° C.

The $PF_{02}$ P-decomposer strain was found to exhibit a substantial ability to decompose phosphate rock. Whereas the original $PF_{01}$ Bacillus could produce 0.2 mg phosphoric acid per ml of $PF_{01}$ culture per day, the $PF_{02}$ strain produced 360 mg phosphoric acid per ml of culture per day.

The $PF_{02}$ bacteria contains 17 integrated copies of the *Bacillus megaterium phosphaticum* phosphate-decomposing genes.

As indicated above, TLB containing the $PF_{02}$ strain was deposited with the American Type Culture Collection.

EXAMPLE 5

Construction of the Potassium Decomposing Bacteria of TLB

The $GN_{02}$ N-fixer bacterium also requires potassium to sustain its metabolism. In order to address this requirement, a recombinant bacteria was produced that had the ability to solubilize (i.e. decompose) the potassium contained in potassium rock. The bacterium was constructed by transforming a *Streptomyces jingyangensis* isolate with DNA obtained from a natural isolate of *Bacillus mucilagneosus* var. Krassilnikov. The Bacillus isolate was obtained from a sample of weathered potassium rock.

*Bacillus mucilagneosus* var. Krassilnikov is widely distributed in weathered potassium ore fines that are present around potassium mines. The bacterium can use a wide variety of organic substances as nutrients. The strain is chemoheterotrophic and facultatively anaerobic. At the end of its oxidative metabolic chain, the bacterium uses molecular oxygen as the electron acceptor. During metabolism, a thick slime layer is produced outside the cell wall, which is believed to contain the enzymes that decompose the potassium rock. The mechanism of decomposition is not yet clear. The G+C content of the cells is 52 mol % (Tm).

A. Culturing of the Natural Potassium Decomposing Bacterium

To isolate the bacterium, a sample of weathered potassium rock was pulverized to about 200 mesh, and added to a sterilized culture medium containing 10.0 g saccharose, 1.0 g ground weathered phosphate rock, 2.0 g diammonium phosphate, 2.0 g $MgSO_4.7H_2O$, 2.0 g $Na_2SO_4.10H_2O$, 1.0 g yeast extract powder, 1.0 ml activator, per liter of soil solution. The culture medium was prepared without activator and autoclaved for 40 minutes. The activator and phosphate rock were added to the medium after the medium had been cooled to 50° C.

The culture was grown for 6 hours at 28-30° C. It was then placed in the special EM radiation chamber and grown under irradiation for 8 hours at 29±1° C., which resulted in the isolation of a potassium decomposing bacterium, designated $KF_{01}$. The isolation procedure was repeated three times, which had the effect of increasing the purity of the culture and the energy level of the microorganisms. The culture was sealed and stored at 0±1° C.

The strain was enriched for variants adapted to artificial culture medium in the following manner. Approximately 20-50 ml of $KF_{01}$ cells was added to a culture medium containing 12 g saccharose, 5-10 g weathered potassium rock powder, 1.0 g $(NH_4)_2SO_4$, 1.0 g activator, 1.0 g $MgSO_4.7H_2O$, 1.0 g $Na_2SO_4.10H_2O$, per liter of soil solution. The culture medium was prepared without activator and autoclaved for 40 minutes. The activator and phosphate rock were added to the medium after the medium had been cooled to 50° C.

The culture was then grown under the appropriate EM field for 9 hours at 28°-30° C. The EM field was then switched off and the culture grown another 72 hours at 28±1° C. The final $KF_{01}$ concentration was $10^6$-$10^8$/ml. The culture was stored at 0±1° C.

The $KF_{01}$ isolate was found to be rod shaped, 0.6-0.8× 1.0-1.6 μm in size. Older cells of the isolate could form spores and could survive long periods of dry soil and/or low temperatures. When ambient conditions became favorable, they slowly revived.

B. Construction of a Potassium Decomposing Derivative of *Streptomyces jingyangensis*

The isolate used as the recipient of DNA from *Bacillus mucilagenosus* var. Krassilnikov was *Streptomyces jingyangensis*. The recipient bacterium was designated $FS_{04}$.

The *Streptomyces jingyangensis.* strain was conditioned by growth in a culture medium containing 10.0 g potato starch, 2.0 g activator, 2.0 g $KH_2PO_4$, 2.0 g $K_2HPO_4$, 1.5 g $MgSO_4.7H_2O$, 1.5 g $Na_2SO_4.10H_2O$, 0.01 g $FeSO_4.7H_2O$. The culture medium was prepared without activator and autoclaved for 30 minutes. The activator was added to the medium after the medium had been cooled to 60° C. The culture medium was divided into four 500 ml Erlenmeyer flasks; the microbial inoculum was 30-50 ml, and was added to the medium after the medium had cooled below 40° C. The flasks were then exposed to the EM field specific to the $FS_{04}$ strain for 12 hours at 26±1° C. The EM field was then switched off and the culture continued for 72 hours at the same temperature. The final $FS_{04}$ concentration, thus enriched, reached $10^8$-$10^{10}$ cells/ml. The enriched culture was sealed and stored at 0±1° C.

DNA of *Bacillus mucilagneosus* var. Krassilnikov that encoded the potassium decomposing enzymes of the bacteria were transferred to the $FS_{04}$ strain using a temperate bacteriophage lambda ($D_{02}$). Temperate bacteriophage lambda ($D_{02}$) was inoculated into a liquid culture of the $KF_{01}$ strain and cultivated at 26±1° C. under EM field parameters suitable for the replication of the $D_{02}$ phage's host cells. Growth was stopped when the concentration of $D_{02}$ lysogenic bacteria reached $10^6$ cells/ml.

Approximately 500 ml of the culture was then placed in the incubation chamber of the EM irradiation apparatus. The EM field parameters were then readjusted to stimulate the replication of the $D_{02}$ phage DNA in the host cells and their ultimate lysis. This cultivation continued for about 9 hours. After lysis, a large amount of modified $D_{02}$ phage was present.

The $C_{02}$ phage were adapted to the $PF_{01}$ host in the following manner. $PF_{01}$ cells were cultured in 250 ml of medium containing (per liter) 10 g ground weathered phosphate rock, 1000 ml soil solution, 5.0 g saccharose, 15.0 g starch, 2.0 g $MgSO_4.7H_2O$, 2.0 g $Na_2SO_4.10H_2O$, 1.0 g activator. Prior to inoculation, all of the media ingredients, except for the activator, had been mixed, autoclaved for 30 minutes and then cooled to 70° C. Activator had then been added, and medium was then divided equally among several 500 ml Erlenmeyer flasks. The flasks were shaken continuously for 8 hours at about 27° C. At the end of the 8 hours, the flasks were placed in an EM field specific to the PF strain and the culture was grown for another 6 hours. At the end of the 6-hour growth period, 20–30 ml of the phage culture and one gram of activator were added to each flask. The resulting mixtures were let stand for 3 hours at about 27° C.

At the end of the 3-hour resting period, the flasks were placed in the EM field and grown for another 4 hours, at which time almost all the $PF_{01}$ cells had been infected by the $C_{02}$ phage.

The EM field parameters were changed and the culture was exposed briefly for 10–15 minutes. The EM field parameters were then reset to the values initially employed. The culture was grown under this condition until almost all the $PF_{01}$ cells had been lysed by the $C_{02}$ phage. The resulting $C_{02}$ culture was sealed and stored at 0±1° C.

The $D_{02}$ phage's ability to infect the $KF_{01}$ strain was enhanced in the following manner. $KF_{01}$ cells were cultured in medium containing 8.0 g saccharose, 1.0 g yeast extract, 1.0 ml activator, 16.0 g corn starch, 2.0 g $MgSO_4.7H_2O$, 2.0 g $Na_2SO_4.10H_2O$, 2.0 g diammonium phosphate, 8.0 g weathered potassium rock. All of the culture medium ingredients except the activator were mixed well and autoclaved 30 minutes. After cooling to about 40° C., the mixture was divided into four 500 ml Erlenmeyer flasks, then 1 ml activator and 50 ml of the $KF_{01}$ culture were added.

The flasks were shaken continuously for four hours at 25±1° C. After shaking, the flasks were exposed to an EM field of parameters specific to the $KF_{01}$ strain (as indicated above) for another 3–5 hours, at the end of which time the $KF_{01}$ concentration was $10^9$/ml. At the conclusion of this step, 20 ml of the $D_{02}$ phage culture was added.

The EM field parameters were reset and the culture grown in this field for 22 hours, at the end of which time the field was switched off. The culture was then grown for another 56 hours without radiation. At this stage, almost all the $D_{02}$ phages had infected $KF_{01}$ cells. The EM field was then readjusted to new parameters and the culture grown in the new field for 10–15 hours, at the end of which time the $KF_{01}$ cells had lysed and a large amount of phage had been released. The phage culture was sealed and stored at about −1° C.

The recipient $FS_{04}$ bacterium was infected with the $D_{02}$ phage as follows. Approximately 50 ml of the $FS_{04}$ culture was inoculated into each of several 500 ml Erlenmeyer flasks that contained 250 ml of medium containing (per liter): 10.0 g ground weathered potassium rock, 1000 ml soil solution, 1.0 g yeast extract powder, 5.0 g saccharose, 10 g corn starch, 2.0 g $MgSO_4.7H_2O$, 2.0 g $Na_2SO_4.10H_2O$, 0.01 g $FeSO_4$, 2.0 g diammonium phosphate, 1.0 ml activator.

The culture medium ingredients except for the activator were mixed well and autoclaved for 30 minutes. The sterile medium was then cooled to 40° C. and the activator was added.

The culture was grown at the temperature appropriate to the $FS_{04}$ strain for 3 hours. The culture was then transferred to the special cultivation chamber of the electroporator. At the required frequency and potential, the porator was cycled on-off three times; the intervals being not longer than 6 seconds. During this operation, the temperature was held at 2°–3° C.

Immediately thereafter, 30 ml of the $D_{02}$ phage culture was added to each flask followed by 1 ml activator. The temperature of the culture was allowed to rise slowly to about 27° C. over 3 hours. The flask cultures were then grown at that same temperature under an EM field of parameters specific to this operation, as indicated above. The action of the EM field was to suppress and kill undesired variants and permit the desired variants to survive. The EM field parameters were then again readjusted and the culture grown for another 4½ hours. This last EM field stimulated the transduction of the operative gene DNA into the $FS_{04}$ cells and its integration into the $FS_{04}$ genome. The final culture (designated $KF_{02}$) was sealed and stored at temperatures below 4° C.

The recombinant potassium decomposing strain was found to possess a strong K-decomposing ability, representing an increase in K production from the 1.8 mg per ml of the $KF_{01}$ culture per day, to 28.8 mg per ml per day for the $KF_{02}$. These values were obtained in the laboratory; field tests have shown that the K-decomposer's efficiency is even higher.

The $KF_{02}$ bacteria contains 19 integrated copies of the *Bacillus mucillagenosus* var. Krassilnikov.

As indicated above, TLB containing the $KF_{02}$ strain was deposited with the American Type Culture Collection.

EXAMPLE 6

Production of Wheat Bran Containing Growth Factors Provided by a Growth Factor-Producing Yeast Strain The yeast strain *Saccharomyces diastaticus* ferments starch residues in wheat bran to thereby produce a vitamin-B complex. The activity of the strain was enhanced for use in providing nutrient growth factors to the above-described microbial components of the TLB fertilizer strain.

The initial *Saccharomyces diastaticus* isolate was designated $PX_{01}$. Approximately 300 g autoclaved wheat bran (having a residual starch content of not less than 10%) was placed in a 2 liter beaker. Approximately 5 g of $PX_{01}$ yeast were added to 420 ml water and mixed well. The two mixtures were combined and stirred well.

The culture was grown for 9 hours at 35° C., then subjected to 60 minutes radiation in the EM field at field parameters specific to this procedure. The resulting yeast was designated $PX_{02}$.

Wheat bran containing the $PX_{02}$ yeast was dried at 45° C. and stored in a dry, sterile environment.

The required growth factors were obtained by the fermentation of starch residues in wheat bran by the $PX_{02}$ yeast. The procedure for producing such growth factor is described below.

Approximately 10 kg of autoclaved dry wheat bran was mixed with 500 g of the above-described wheat bran containing the $PX_{02}$ yeast and additional water at 35° C. was added and mixed well. This culture was grown for 9 hours at 35–37° C. under the EM field specific to this procedure. Approximately 100 kg of dry wheat bran and additional water at 35° C. was added and mixed in thoroughly. The mixture was then cultured for another nine hours at 35°–37° C. under semi-anaerobic conditions. A large amount of $PX_{02}$ yeast was thereby produced.

The above-described cultivation was repeated using progressively greater amounts of wheat bran. The ratio of wheat bran containing the $PX_{02}$ yeast to the added bran was maintained at 5:100 during the repeated fermentation cycles. When the desired volume was attained, the bran was fermented for 9 hours, after which it was dried at a temperature not higher than 45° C. The resulting wheat bran containing vitamin B complex thus obtained was used in TLB.

EXAMPLE 7

Production of Wheat Bran Containing High Energy Molecules Provided by an ATP-Producing Yeast Strain In order to enhance the production of ATP, a strain of *Saccharomyces sinerises* Yue (designated $MX_{01}$) was employed. Approximately 300 g of wheat bran was placed in a 2 liter beaker and autoclaved 30 minutes. Approximately 5–10 g of the $MX_{01}$ dry yeast and 500 ml sterilized water were added to the beaker and mixed well. The beaker was then covered with 6 layers of dampened cloth and the culture grown for 9 hours at 35°–37° C. under EM field of parameters suitable for this procedure. The resulting yeast was designated $MX_{02}$. The $MX_{02}$ yeast was dried with the wheat bran at a temperature below 45° C. and stored.

The $MX_{02}$ yeast was used to ferment wheat bran for about 9 hours at 35°–37° C. More dry wheat bran was added to the $MX_{02}$ mixture and fermentation continued at the same temperature for another 60 minutes, which produced pyruvic acid by the following mechanism:

$$C_6H_{12}O_6 + 2NAD + 2Pi + 2ADP$$

$$\downarrow$$

$$2CH_3COCOOH + 2NADG_2 + 2ATP$$

$$\downarrow$$

$$CH_3COCOOH + Pi \rightarrow CH3CO \sim Pi + CO_2 + 2(H^+)$$

$$\downarrow$$

$$CH_3CO \sim Pi + ADP \rightarrow ATP + CH_3COOH$$

The phosphate ions in the above reactions come mainly from the phosphate that results from the decomposition of phosphate rock by the P-decomposer bacterium.

The resulting wheat bran containing enriched high energy molecules thus obtained was used in TLB.

EXAMPLE 8

Production of a TLB Microbial Fertilizer

A TLB fertilizer was prepared. The fertilizer possessed a core, an intermediate layer, and a film layer.

The core was composed of:

(1) powdered rock phosphate—65–70 parts by weight of powdered rock phosphate (containing 25% or more phosphorus, calculated as $P_2O_5$) ground to 200 mesh;

(2) fermented wheat bran—28—32 parts by weight of fermented wheat bran. The fermentation bacteria was vitamin B fermentation bacteria produced by the Shanghai 12th Pharmaceutical Factory, however, equivalent microbes may be employed. The weight ratio of fermentation bacteria to wheat bran was 1:10. The fermenting temperature was 28–37° C. Fermentation was for 9–12 hours; and (3) bittern—28–32 parts by weight of bittern (containing 50% $Na_2SO_4.10H_2O$ and 50% $Mg_2SO_4.7H_2O$).

The intermediate layer was composed of:

(1) powdered weathered coal or coal-waste—65–70 parts by weight of weathered coal or coal-waste (weathering degree over 80%, burning loss over 35%);

(2) fermented wheat bran—15–18 parts by weight of fermented wheat bran. The fermentation bacteria is pyruvic acid fermentation bacteria made by Beijing Brewery Factory, however, equivalent microbes may be employed. The weight ratio of fermentation bacteria to wheat bran was 1:10. The fermenting temperature was 30°–37° C. Fermentation was for 9–12 hours; and (3) bittern—0.5–1 part by weight of bittern (containing 50% $Na_2SO_4.10H_2O$ and 50% $Mg_2SO_4.7H_2O$);

(4) chalk soil or lime—1.5–2 parts by weight of chalk soil or lime.

The film layer was composed of:

(1) powdered talc—2–3 parts by weight of powdered talc (2) bone glue—0.2–0.5 parts by weight of bone glue the ratio of talc powder+ bone glue to water was between 1:7 and 1:10

The ratio of granule core to intermediate layer to outer film layer was (24–28):(72–76):2. The diameter of the core layer was 1.8–1.9 mm; the thickness of the intermediate layer was 0.7–0.9

The granules were prepared using either of the following procedures:

Procedure 1

Step 1: Preparation of the core layer:

Grind 67 kg of rock phosphate containing 30% phosphorus in a suitable grinder then pulverize in a suitable pulverizer until all the material can pass through a 200 mesh sieve.

Place 30 kg of wheat bran and 1 kg Vitamin B fermentation bacteria produced by the Shanghai 12th Pharmaceutical Factory or equivalent in a suitable fermentation tank. Ferment the mixture at 32° C. for 10 hours. Place the fermented mixture in a mixer and mix thoroughly with 30 kg of bittern, dry the homogenized mixture at 45° C. for 10 minutes, then pulverize the mixture in a suitable pulverizer until all the material can pass through a 100 mesh sieve.

Mix together the powdered rock phosphate, fermented wheat bran, and powdered bittern then form into granules of diameter averaging about 1.86 mm. Step 2: Preparation of the intermediate layer:

Grind 67 kg of weathered coal (degree of weathering 85%, burning loss 42%). in a suitable grinder, then pulverize in a suitable pulverizer until all the material can pass through a 200 mesh sieve.

Place 16 kg of wheat bran and 1.6 kg of pyruvic acid fermentation bacteria made by the Beijing Brewery Factory or equivalent in a suitable fermenting tank. Ferment the mixture at 35° C. for 10 hours. Dry it at 50° C. for 10 minutes. Mix it with 0.5 kg of bittern and 1.5 kg of chalk soil.

Step 3: Granulation:

Form 25 kg of the core material prepared in Step 1 into granules in a suitable granulator, add 75 kg of intermediate layer material prepared in Step 2 to the granulation process, then form an outer film layer over the granule by spraying it with an aqueous solution of 2 kg powdered talc, 0.3 kg bone glue and 21 kg water and finally dry the resulting granules at <65° C. for 10 minutes. The result is a high-efficiency universal microbial fertilizer, in a granule diameter of about 3.5 mm.

Procedure 2

Procedure 2 is conduced in the same manner as procedure 1 except that the weathered coal in the intermediate layer was replaced with coal-mine waste and the chalk soil was replaced with lime, resulting in a granule diameter of about 3.4 mm.

After analysis by appropriate institutions, such as the Beijing Forestry University, the Beijing University, the Beijing Normal University, the Beijing Agriculture University and the China Forestry Academy, the nitrogen-fixing capability of the intermediate layer of the fertilizers produced in both Procedures 1 and 2 was 100 μmol/g (at 8 days), and the nitrogen-fixing capability of the intermediate layer was 100 μmol/g.

The above-described high-efficiency universal microbial fertilizer was tested in field experiments with tobacco, grapes, apples, wheat, late rice; and corn. All crops obtained high yields. Thus, the advantages of TLB include (1) it uses raw materials that are abundant, (2) the manufacturing process is simple, (3) the fertilizer increased yields of all kinds of plants, and (4) the fertilizer is avirulent, non-toxic and non-polluting.

EXAMPLE 9

Production of a TLB Microbial Fertilizer

A high-efficiency, sustained-release microbial fertilizer was manufactured that employed bacteria to fix nitrogen ($N_2$) and decompose immobilized phosphorous, potassium and organic compounds, thereby supplying nitrogen, phosphorous, potassium and other nutrients required by plants. The bacteria used in the process were engineered by recombinant DNA procedures. The donor of the nitrogen-fixing DNA segment was *Alcaligenes faecalis*; the donor of the phosphorus-decomposer DNA was *Bacilllus megaterium phosphaticum*; the donor of the potassium-decomposer DNA was *Bascillus mucilagenosus* var. Krassilnikov; and that of the coal-decomposer was *Polyangium cellulosum*. The recipient organism for all four donated DNA segments was *Streptomyces jingyangensis*. These four engineered microorganisms establish a symbiotic relationship wherein the nitrogen-fixer supplies nitrogen required as nutrient by the other three, which in turn supply the phosphorus, potassium and carbohydrates required by the nitrogen-fixer and themselves. No one of these organisms can, by itself, conduct the desired level of metabolic activity outside the symbiotic community.

The fertilizer was prepared according to the following method.

Step 1. Grind rock phosphate with a phosphorus content of greater than 25 percent to 80 mesh.

Step 2. Prepare a bacterial agent containing 2 to 4 billion phosphorus-decomposer bacterial per gram and 2 to 4 billion potassium-decomposer bacteria per gram.

Step. 3. Combine 500 to 1000 grams of the bacterial agent prepared above with 100 kilograms powdered rock phosphate prepared under Step 1 and mix homogeneously.

Step 4. Dry carbonaceous material such as weathered coal, coal-mine waste (gangue), straw charcoal soil, oil shale, petroleum residues or similar matter at a temperature not greater than 500° C. until the water content is reduced to less than 12 percent and grind it to powder with grain size 80 mesh.

Step 5. Add 120 to 300 grams of bacterial agent containing 2–4 billion nitrogen-fixer bacteria per gram and 2–4 billion carbon-decomposer bacteria per gram at a ratio of 120 to 300 grams bacterial agent to 100 kilograms of the dry carbonaceous material and mix and stir homogeneously.

Step 6. Mix rock phosphate containing phosphorus-decomposer bacteria and potassium-decomposer bacterial with the carbonaceous material containing nitrogen-fixer bacteria and carbon-decomposer bacteria at the ratio of 1 to 2–3 by weight and stir homogeneously.

Step 7. Dry at a temperature not greater than 100° C. until the water content is less than 12%. The resulting product is microbial fertilizer in powder form which can be either packaged as such or made into granules. The granular form is prepared after the conclusion of Step 6 by forming granules of diameter 1 to 5 millimeters and drying at a temperature less than 100° C.

The fertilizer was manufactured as indicated in Procedure A or Procedure B.

Procedure A

Step 1. Grind 100 kilograms rock phosphate with a phosphorus content greater than 25 percent (as $P_2O_5$) to grain size 80 mesh.

Step 2. Add 800 grams of bacterial agent containing 3 billion phosphorus-decomposer bacteria per gram and 3 billion potassium-decomposer bacteria per gram to the 100 kilograms of ground rock phosphate powder from Step 1 and mix and stir homogeneously.

Step 3. Dry 350 kilograms weathered coal or coal-mine waste containing 25 percent carbon at a temperature of 400° C. until the water content is 10 percent.

Step 4. Grind the carbonaceous matter from Step 3 to 80 mesh.

Step 5. Add 1000 grams of bacterial agent containing 4 billion nitrogen-fixer bacteria per gram and mix and stir homogeneously.

Step 6. Combine-the rock phosphate mixture prepared under Step 2 with the carbonaceous matter-nitrogen-fixer bacteria mixture from Step 5 in a ratio of 1 to 3 by weight and stir homogeneously. Dry at a temperature of 100° C. until the water contents is 10%. The result is microbial fertilizer in powder form.

Procedure B

Step 1. Grind 100 kilograms rock phosphate with a phosphorus content greater than 25 percent (as $P_2O_5$) to grain size 80 mesh.

Step 2. Add 500 grams of bacterial agent containing 2 billion phosphorus-decomposer bacteria per gram and 2 billion potassium-decomposer bacteria per gram to the 100 kilograms of ground rock phosphate powder from Step 1 and mix and stir homogeneously.

Step 3. Dry 350 kilograms straw charcoal soil containing 30 percent carbon at a temperature of 450° C. until the water content is 11 percent.

Step 4. Grind the carbonaceous matter from Step 3 to 80 mesh.

Step 5. Add 500 grams of bacterial agent containing 5 billion nitrogen-fixer bacteria per gram and 5 billion carbon-decomposer bacteria per gram and mix and stir homogeneously.

Step 6. Combine the rock phosphate mixture prepared under Step 2 with the carbonaceous matter-nitrogen-fixer bacteria mixture from Step 5 in a ratio of 1 to 2 by weight and stir homogeneously.

Step 7. Place resulting mixture in a granule-making machine and form into granules of 2 millimeters diameter.

Step 8. Dry at a temperature of 85° C. until the water contents is 10 percent. The result is microbial fertilizer in powder form.

The resulting biological fertilizer produced by either Procedure A or Procedure B was avirulent, non-toxic and long acting. One application has been generally found to meet plant nutrition requirements for an entire growing season. The fertilizer has been proved by field experiments which were conducted by the Plant Research Institute, the Fruit Tree Research Institute, the Tobacco Research Institute of China, and the Academy of Agriculture Science, the Beijing Agricultural College. All crops tested (wheat, paddy rice, fruit or vegetable crops) have shown manifest increases in yields. In addition, the product has other advantages such as labor savings, time saving and long-term fertilizing effect.

After testing of the fertilizer by the Beijing University, the Quinghua University, the Beijing Normal University, the Beijing Agriculture University, the Beijing Forestry University and the Chinese Academy of Forest Science, it was found that its nitrogen-fixing activity of the eighth day was equal or greater to 100 μmol/gram (determined by the acetylene reduction method, discussed below).

EXAMPLE 10

Method of Detecting and Measuring Biological Nitrogen Fixation

One aspect of the present invention concerns a method of detecting and measuring biological nitrogen fixation which is particularly useful in conducting research on biological nitrogen fixation, identification of nitrogen-fixing microorganisms, and determination of the value of nitrogen-fixing agents and microbial fertilizers.

Much research is being devoted to biological nitrogen fixation and it ranks high among the major research areas given prominence in the developed countries. Research in this area requires a means of identifying microorganisms and plants with nitrogen-fixing capability, mapping of nitrogen-fixing DNA, classifying the functions of nitrifler bacteria, quantitatively determining the nitrogen-fixing efficiency of various nitrogen-fixers, and determining the nitrogen-fixing efficiency of microbial fertilizers. These activities require a method with high sensitivity, accuracy and reliability.

Several methods have been developed to assay for reduced nitrogen. The earliest technique for measuring nitrogen reduction was the Kjeldahl method, which is accurate and reliable, but has such low sensitivity that it cannot detect the small values involved in biological nitrogen fixation. The nitrogen isotope, $^{15}N$ has also been used to measure nitrogen reduction. Although the method is about 1000 times more sensitive than the Kjeldahl method, it is still not satisfactory because it requires salts containing $^{15}N$ and other chemicals which are expensive and also requires the use of isotopic mass spectrography.

More recently, an acetylene-reduction method was developed, which is as much as 1,000 times more sensitive than the $^{15}N$ method, i.e. as much as $10^6$ times more sensitive than the Kjeldahl method. The technique measures the reduction of acetylene to ethylene, and is based on the premise that the nitrogen-fixation enzyme of a microorganism which converts:

$$N\equiv N \rightarrow 2NH_3$$

is also be able to reduce the triple bond (i.e., $C\equiv C$ bond) of acetylene to form ethylene:

$$C\equiv C \rightarrow CH_2=CH_2$$

This technique has enabled scientists to identify more than 400 species of nitrogen-fixing microorganisms in over 70 genera. Because this method does not detect nitrogen directly but determines the quantity of ethylene formed from acetylene, the method has been considered suitable only for qualitative analyses and not for quantitative determinations.

One aspect of the present invention is thus an extension of the acetylene reduction assay so as to provide a quantitative method of analyzing nitrogen fixation. In accordance with this method, a nitrogen fixation sample is placed in a chamber (such as a culture flask) of appropriate capacity, and an appropriate amount of carbohydrate of less than 10 carbons is added with sterile water. The chamber is sealed, as with a rubber stopper, and the culture is maintained for a certain time at an appropriate temperate. The mixed gas evolved from the culture is extracted from the chamber, and evaluated by gas chromatography. The method provided the following advantages: (1) high sensitivity, accuracy and reliability in determining quantitative levels of nitrogen fixation; (2) simplicity, feasibility, low cost, and high visualization; (3) producing not only qualitative readings of nitrogen-fixation but also quantitative values. This method can be used for rhizobial bacteria, free-living nitrogen-fixer bacteria, and related bacterial agents and fertilizer made from them.

The nitrogen fixation capacity of TLB was evaluated using different carbon sources as described in the following procedures. In each procedure, an appropriate amount of the test sample (pure nitrogen-fixer microorganisms, a suspension of nitrogen-fixer microbes, nitrogen-fixing bacterial agents or products) was placed into a culture flask of suitable capacity, and an appropriate amount of corresponding culture medium was added. The flask was sealed with a rubber stopper. Air was evacuated, and the flask was filled with a standard gas mixture containing 20% $O_2$ and 80% $N_2$, (ambient air may alternatively be used directly without the vacuum-pumping step) until the pressure in the bottle was one atmosphere. The prepared culture flask was maintained at an appropriate temperature (normally 10°–40° C.) and cultured for a time appropriate to the requirements of the nitrogen-fixer microbes and products being tested. The sample was evaluated using a standard sampler to determine the change in $N_2$ percentage. This change was used to calculate the decrease of $N_2$, and from that value, the quantity of nitrogen fixed per gram of nitrogen-fixer microorganisms and/or products was determined.

Procedure 1: Determination of nitrogen fixation capacity of TLB using cane sugar as the carbon source 1. An amount of TLB microbial fertilizer was ground to 60 mesh or finer.

2. Approximately 0.5–1.0 g TLB was placed in a 100 ml culture flask, 0.25–1.0 gram of cane sugar was added, and the flask was filled with 2–10 ml sterile water, and sealed with a rubber stopper.

3. The air was evacuated from the flask prepared in step 2. The flask was then filled with a gas mixture containing 20% $O_2$ and 80% $N_2$ until the pressure in the flask reached one atmosphere (the volume of gas was about 90–98 ml). The gas mixture of the sample was immediately sampled using a standard sampler, and was tested by gas chromatography. The amount of $N_2$ in the flask was calculated, and designated as "$V_1$." After culturing the flask for 2–10 days at 28° C. ±1° C., the gas mixture was again sampled, tested by gas chromatography, and the amount of $N_2$ in the flask was calculated, and designated as "$V_2$."

4. An uninoculated control was processed as in step 3, and the amount of $N_2$ present in the flask at the start of the test was determined and designated as "$M_1$." The amount of $N_2$ in the flask at the conclusion of the experiment was also determined, and was designated $M_2$. Generally, the difference between $M_1$ and $M_2$ was very small, about 1–2%.

5. The decrease in $N_2$ amount was calculated using the following formula. The actual amount of nitrogen fixed, after subtracting the blank natural decrease, was designated Vm.

$$V_m = [V_1 - V_2 - (M_1 - M_2)]/0.5 - 1.0 \text{ g}$$

By calculation, one gram of TLB fertilizer was found to have fixed over 100 mg of nitrogen. Thus, over 560 mg of nitrogen were fixed per gram of sugar consumed.

Procedure 2: Determination of Nitrogen fixation capacity of rhizospher nitrifying bacteria using glucose as the carbon source.

1. Approximately 0.1–1 g of nitrifying bacteria complex from plant rhizospere was placed in a culture flask of 20ml capacity, 0.1–1.0 gram of glucose was added, and the flask was filled with 2–10 ml sterile water, and sealed with a rubber stopper.

2. The air was evacuated from the flask prepared in step 1. The flask was then filled with a gas mixture containing 20% $O_2$ and 80% $N_2$ until the pressure in the flask reached one atmosphere. 10–100 µl of the gas mixture of the sample was immediately sampled using a standard sampler, and was tested by gas chromatography. The amount of $N_2$ in the flask was calculated, and designated as "$V_2$." After culturing the flask for 6–24 hours at 15°–40° C., 10–100 µl of the gas mixture was again sampled, tested by gas chromatography, and the amount of $N_2$ in the flask was calculated, and designated as "$V_2$."

3. An uninoculated control was processed as in step 2, and the amount of $N_2$ present in the flask at the start of the test was determined and designated as "$M_1$." The amount of $N_2$ in the flask at the conclusion of the experiment was also determined, and was designated $M_2$.

4. The decrease in $N_2$ amount was calculated using the following formula. The actual amount of nitrogen fixed, after subtracting the blank natural decrease, was designated $V_m$.

$$V_m = [V_1 - V_2 - (M_1 - M_2)]/0.1 - 1.0 \text{ g}$$

The amount of nitrogen produced was substantially less than that obtained using TLB.

EXAMPLE 11

Production of a TLB Microbial Fertilizer

TLB fertilizer was prepared using an alternative procedure. The formulation used the above-described microbial strains, and was characterized as having:

a. a granular core manufactured by grinding rock phosphate to 200 mesh; fermenting wheat bran with Vitamin B fermentation bacteria (weight ration=10:1) at 28–37° C. for 9–12 hours; drying mixture of fermented wheat bran and bittern as 45° C.; forming the dried mixture into granules of diameter=1.8–1.9 mm;

b. an intermediate layer manufactured by grinding weathered coal or coal-mine waste to 200 mesh; fermenting wheat bran with pyruvicacid fermentation bacteria (weight ratio =10:1) at 30°–37° C. for 9–12 hours; drying a mixture of fermented wheat bran, bittern and chalk soil or lime at less than 50° C.; forming the resulting mixture into a layer 0.7–0.9 mm thick around the granular core produced above; and c. an outer film layer manufactured by spraying an aqueous solution of bone glue and powdered talc on the surface of the intermediate layer.

The fertilizer was manufactured as follows:

Step 1. Grinding rock phosphate containing nutrient compounds into fine powder, mixing it with fermented wheat bran, bittern (composed mostly of sodium sulfate and magnesium sulfate), then forming it into a spherical granular core.

Step 2. Grinding weathered coal or coal-mine waste into powder, mixing it with wheat bran, bittern, lime or chalk soil and forming it into a layer around the spherical granular core.

Step 3. Spraying and coating the granule formed with an aqueous solution of powdered talc and bone glue to form a film layer which creates a granule with a three-layer structure. The purpose of incorporating rock phosphate in the core layer was to facilitate the biological decomposition of the phosphate rock and to prevent the phosphorus from being fixed by reacting with metal cations in the ambient soil. The purpose of the intermediate layer was to facilitate the fixation of nitrogen. The main purpose of sodium sulfate and magnesium sulfate in the core layer and the intermediate layer is to promote bacterial metabolism and photosynthesis in plants. The main purposes of the outer film layer are to limit the passage of oxygen into the granule and protect nitrogen-fixing microorganisms from damage by oxygen to protect the structural integrity of the inner layers structure and to create a closed metabolic environment.

The specific steps for producing the fertilizer are as follows (proportions are by weight):

Core

Powdered rock phosphate 65–70 parts (ground to 200 mesh, phosphorus content not less than 25% by weight).

Fermented wheat bran: 28–32 parts. The fermenting agents Vitamin B fermentation bacteria produced by the Shanghai 12th Pharmaceutical Factory or equivalent. The weight ratio of fermentation bacteria to wheat bran is 1:10. Fermenting temperature is 28°–37° C. Time 9 to 12 hours.

Bittern: 28–32 parts containing 14–16 parts by weight sodium sulfate 10-hydrate and 14–16 parts by weight magnesium sulfate 7-hydrate.

Intermediate Layer

Powdered weathered coal or coal-mine waste ground to 200 mesh, 65–70 parts. Degree of weathering over 80%, burning loss over 35%.

Fermented wheat bran: 15–18 parts. The fermenting agent is pyruvic acid fermentation bacteria made by the Beijing Brewery Factory or equivalent, weight ratio of bacteria to wheat bran 1:10, fermentation temperature 30°–37° C., time 9–12 hours.

Bittern: 0.5–1 part containing one-half sodium sulfate 10-hydrate and one-half magnesium sulfate 7-hydrate.

Chalk soil (or lime) 1.5–2 parts.

Film Layer

Powered talc: 2–3 parts; Bone glue 0.2–0.5 parts; ratio talc powder+bone glue to water=1:(7–10).

Ratio of granule core to intermediate layer to outer film layer=(24–28): (72–76): 2. Diameter of the core layer= 1.8–1.9 mm, thickness of intermediate layer=0.7–0.9 mm.

The following procedures describe two methods of preparing the invention without, however, limiting other methods.

Procedure 1

Preparation of the core layer:

Grind 67 kg of rock phosphate containing 30% phosphorus in a suitable grinder, the pulverize in a suitable pulverizer until all the material can pass through a 200 mesh sieve.

Place 30 kg of wheat bran and 1 kg Vitamin B fermentation bacteria produced by the Shanghai 12th Pharmaceutical Factory or equivalent in a suitable fermentation tank. Ferment the mixture at 32° C. for 10 hours. Place the fermented mixture in a mixer and mix thoroughly with 30 kg of bittern, dry the homogenized mixture at 45° C. for 10 minutes then pulverize the mixture in a suitable pulverizer until all the material can pass through a 100 mesh sieve.

Mix together the powered rock phosphate, fermented wheat bran and powdered bittern then form into granules of diameter about 1.86 mm.

Preparation of the intermediate layer:

Grind 67 kg of weathered coal (degree of weathering 85%, burning loss 42%), in a suitable grinder, then pulverize in a suitable pulverizer until all the material can pass through a 200 mesh sieve.

Place 16 kg of wheat bran and 1.6 kg of pyruvic acid fermentation bacteria made by the Beijing Brewery Factory or equivalent in a suitable fermenting tank. Ferment the mixture at 35° C. for 10 hours. Dry at 50° C. for 10 minutes and mix it with 0.5 kg of bittern and 1.5 kg of chalk soil.

Granulation:

Form 25 kg of the prepared core material into granules in a suitable granulator, add 75 kg of intermediate layer material to the granulation process, then form an outer film layer over the granule by spraying it with an aqueous solution consisting of 2 kg powdered talc, 0.3 kg bone glue and 21 kg water, and finally dry the resulting granules at<65° C. for 10 minutes. The result is a high-efficiency universal microbial fertilizer, in a granule diameter of about 3.5 mm.

Procedure 2

All conditions are the same as in Procedure 1, except that the weathered coal in the intermediate layer is replaced with coal-mine waste, and chalk soil is replaced with lime, resulting in a granule diameter of about 3.4 mm.

After analysis by appropriate institutions, such as the Beijing Forestry University, the Beijing University, the Beijing Normal University, the Beijing Agricultural University and the China Forestry Academy, the nitrogen-fixing capability of the core in Procedures 1 and 2 was found to be 100 µmol/g (8 days), and the nitrogen-fixing capability of the intermediate layer is 100 µmol/g.

The China Agricultural Academy used the high-efficiency universal microbial fertilizer described above in field experiments with tobacco, grapes, apples and wheat; Hu Zhou City, Ze Jiang Province, used it with late rice; the Lo Ping Agriculture, Industrial and Commercial Company of Beijing used it with corn. All obtained high yields.

Thus, the result of either Procedure was a high-efficiency universal microbial fertilizer which was avirulent, non-toxic, non-polluting and which could increase yields of grains, vegetables and fruits.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A microbial fertilizer that comprises a granule comprising
   (A) a central rock phosphate core containing a phosphate rock decomposing bacterium;
   (B) an intermediate layer comprising a carbonaceous material and a source of starch and containing a nitrogen fixing bacterium, a carbon-waste decomposing bacterium, a rock potassium decomposing bacterium, a growth factor producing yeast, and an energy producing yeast; and
   (C) an outer film sufficient to limit the passage of oxygen into the granule.

2. A microbial fertilizer that comprises: (a) a nitrogen fixing bacterium; (b) a carbon-waste decomposing bacterium; (c) a phosphate rock decomposing bacterium; and (d) a rock potassium decomposing bacterium, wherein said bacteria (a)–(d) produce reduced nitrogen, carbon, phosphate and potassium nutrients, respectively, in amounts that augment the growth of plants, and wherein said nitrogen fixing bacterium (a) is *Streptomyces jingyangensis* containing DNA from *Alcaligenes faecalis* and is deposited as a component of ATCC 55597.

3. A microbial fertilizer that comprises:
   (a) a nitrogen fixing bacterium;
   (b) a carbon-waste decomposing bacterium;
   (c) a phosphate rock decomposing bacterium; and
   (d) a rock potassium decomposing bacterium, wherein said bacteria (a)–(d) produce reduced nitrogen, carbon, phosphate and potassium nutrients, respectively, in amounts that augment the growth of plants, and wherein said carbon-waste decomposing bacterium (b) is *Streptomyces jingyangensis* containing DNA from *Polyangium cellulosum* and is deposited as a component of ATCC 55597.

4. A microbial fertilizer that comprises:
   (a) a nitrogen fixing bacterium;
   (b) a carbon-waste decomposing bacterium;
   (c) a phosphate rock decomposing bacterium; and
   (d) a rock potassium decomposing bacterium, wherein said bacteria (a)–(d) produce reduced nitrogen, carbon, phosphate and potassium nutrients, respectively, in amounts that augment the growth of plants, and wherein said phosphate rock decomposing bacterium (c) is *Streptomyces jingyangensis* containing DNA from *Bacillus megaterium phosphaticum* and is deposited as a component of ATCC 55597.

5. A microbial fertilizer that comprises:
   (a) a nitrogen fixing bacterium;
   (b) a carbon-waste decomposing bacterium;
   (c) a phosphate rock decomposing bacterium; and
   (d) a rock potassium decomposing bacterium, wherein said bacteria (a)–(d) produce reduced nitrogen, carbon, phosphate and potassium nutrients, respectively, in amounts that augment the growth of plants, and wherein said rock potassium decomposing bacterium (d) is *Streptomyces jingyangensis* containing DNA from *Bacillus mucilagneosus* var. Krassilnikov and is deposited as a component of ATCC 55597.

6. The microbial fertilizer of claim 1, wherein said growth factor producing yeast is *Saccharomyces diastaticus* of ATCC 55597.

7. The microbial fertilizer of claim 1, wherein said energy producing yeast is *Saccharomyces sinenses* Yue of ATCC 55597.

8. A microbial fertilizer that comprises:

(a) a nitrogen fixing bacterium;

(b) a carbon-waste decomposing bacterium;

(c) a phosphate rock decomposing bacterium;

(d) a rock potassium decomposing bacterium;

(e) a living growth factor producing yeast; and (f) a living energy producing yeast, wherein said bacteria (a)–(d) produce reduced nitrogen, carbon, phosphate and potassium nutrients, respectively, in amounts that augment the growth of plants, and wherein said fertilizer is ATCC 55597.

9. A microbial fertilizer that comprises a granule comprising a central rock phosphate core, an intermediate layer and an outer film, wherein said central rock phosphate core is manufactured by the steps comprising:

(1) grinding rock phosphate to about 200 mesh;

(2) combining said ground rock phosphate with a source of starch fermented by a growth factor producing yeast, and with a rock phosphate decomposing bacterium to form a mixture of said ground rock phosphate, said source of starch fermented by said growth factor producing yeast, and said rock phosphate decomposing bacterium; and (3) drying said mixture of step (2) and forming said dried mixture into granules, and wherein said intermediate layer is manufactured by the steps comprising:

(1') grinding weathered coal or coal-mine waste to about 200 mesh;

(2') combining said ground weathered coal or coal-waste with said source of starch, with said growth factor producing yeast, with an energy producing yeast, with a nitrogen fixing bacterium, with a carbon-waste decomposing bacterium, and with a potassium rock decomposing bacterium to form a mixture of said ground weathered coal or coal-waste, said source of starch, said growth factor producing yeast, said energy producing yeast, said nitrogen fixing bacterium, said carbon-waste decomposing bacterium, and said potassium rock decomposing bacterium; and (3') drying said mixture of step (2') and forming said dried mixture into a layer around the granules of step (3), and wherein said outer film is manufactured by spraying an aqueous solution onto the surface of the intermediate layer formed in step (3') to thereby form an outer film sufficient to limit the passage of oxygen into the granule.

10. The microbial fertilizer of claim 9, wherein:

(i) said nitrogen fixing bacterium is *Streptomyces jingyangensis* containing DNA from *Alcaligenes faecalis* and is deposited as a component of ATCC 55597;

(ii) said carbon-waste decomposing bacterium is *Streptomyces jingyangensis* containing DNA from *Polyangium cellulosum* and is deposited as a component of ATCC 55597;

(iii) said phosphate rock decomposing bacterium is *Streptomyces jingyangensis* containing DNA from *Bacillus megaterium phosphaticum* and is deposited as a component of ATCC 55597; and (iv) said rock potassium decomposing bacterium is *Streptomyces jingyangensis* containing DNA from *Bacillus mucilagenosus* vat. Krassilnikov and is deposited as a component of ATCC 55597.

11. The microbial fertilizer of claim 10, wherein said growth factor producing yeast is *Saccharomyces diastaticus* of ATCC 55597, and wherein said energy producing yeast is *Saccharomyces sinenses* Yue of ATCC 55597.

12. A method of augmenting crop yield of a growing crop selected from the group consisting of cereal crops, fruit crops, vegetable crops and grass crops, which comprises applying the microbial fertilizer of claim 1 to soil that contains said growing crop.

\* \* \* \* \*